United States Patent [19]

Schatz

[11] Patent Number: 5,723,584
[45] Date of Patent: Mar. 3, 1998

[54] BIOTINYLATION OF PROTEINS

[75] Inventor: Peter J. Schatz, Mountain View, Calif.

[73] Assignee: Affymax Technologies N.V., Greenford, United Kingdom

[21] Appl. No.: 383,753

[22] Filed: Feb. 3, 1995

Related U.S. Application Data

[63] Continuation-in-part of Ser. No. 99,991, Jul. 30, 1993, abandoned.
[51] Int. Cl.$^6$ .............................. C07K 19/00; C07K 2/00; C07K 14/00
[52] U.S. Cl. .............................. 530/408; 530/300; 530/345; 530/350
[58] Field of Search .............................. 435/69.7, 172.3; 530/324, 345, 300, 325, 326, 327

[56] References Cited

PUBLICATIONS

Freytag, S.O. et al. *J. Biol. Chem.* 259:12831–12837 (1984).
Murtif, V.L. et al. *PNAS* 82:5617–5621 (1985).
Buoncristiani et al., "Overproduction and Rapid Purification of the Biotin Operon Repressor for *E. coli*," 15 Jan. 1988, *J. Biol. Chem.* 263(2):1013–1016.
Cress et al., "Purification: a one–step nondenaturing purification method for recombinant proteins produced in *E. Coli*," 1993, *Promega Notes* 42:2–7.
Cronan, "The *E. Coli* bio Operon: Transcriptional Repression by an Essential Protein Modification Enzyme," 11 Aug. 1989, *Cell* 58:427–429.
Cronan, "Biotination of Proteins in Vivo," 25 Jun. 1990, *J. Biol. Chem.* 265(18):10327–10333.
Freytag et al., "Molelcualr cloning of a cDNA for human pyruvate carboxylase," *J. Biol. Chem.* 259:12831–12837 (1984).
Lamhonwah et al., "Sequence homology around the biotin-–binding site of human propionyl–CoA carboxylase and pyruvate carboxylase," *Arch. of Biochem. & Biophysics* 254:631–636 (1987).
Murtif et al., "Mutagenesis Affecting the Carboxyl Terminus of the Biotinyl Subunit of Transcarboxylase," 25 Aug. 1987, *J. Biol. Chem.* 262(24):11813–11816.
Reed et al., "*Escherichia coli* exports previously folded and biotinated protein domains," *J. Biol. Chem.* 266:11425–11428 (1991).
Schatz, Peter J., "Use of peptide libraries to map the substrate specificity of a peptide–modifying enzyme: A 13 residue consensus peptide specifies biotinylation in *Escherichia coli*," Bio/Technology 11:1138–1143 (1993).
Shenoy et al., "Effect of mutations at Met–88 and Met–90 on the biotination of Lys–89 of the apo 1.3S subunit of transcarboxylase." *FASEB J.* 2(9):2505–2511.
Shenoy et al., "The Importance of Methionine Residues for the Catalysis of the Biotin Enzyme, Transcarboxylase," 15 Sep. 1992, *J. Biol. Chem.* 267 (26):18407–18412.
Thampy et al., "A rapid purification method for rat liver pyruvate carboxylase and amino acid sequence analyses of NH$_2$–terminal and biotin peptide," *Arch. of Biochem. & Biophysics* 266:270–276 (1988).

*Primary Examiner*—Robert A. Wax
*Assistant Examiner*—Daniel S. Mytelka
*Attorney, Agent, or Firm*—Lauren L. Stevens; Joe Liebeschuetz

[57] ABSTRACT

Biotinylation peptides can be fused to other peptides or proteins of interest using recombinant DNA techniques to provide efficient methods for biotinylating the resulting fusion proteins in vivo or in vitro.

6 Claims, No Drawings

SEQUENCE LISTING ( 1 ) GENERAL INFORMATION:

( i i i ) NUMBER OF SEQUENCES: 102

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(2, 3)
        ( D ) OTHER INFORMATION: /note= "Xaa at position 2 is any
            amino acid; at position 3 is any amino acid other
            than Leu, Val, Ile, Trp, Phe or Tyr."

( i x ) FEATURE:
        ( A ) NAME/KEY: Region
        ( B ) LOCATION: one-of(5, 6, 7, 8)
        ( D ) OTHER INFORMATION: /note= "Xaa at position 5 is Phe or
            Leu; at position 6 is Glu or Asp; at position 7 is
            Ala, Gly, Ser or Thr; at position 8 is Gln or ( i x ) FEATURE:
        ( A ) NAME/KEY: Region
        ( B ) LOCATION: one-of(10, 11, 12, 13)
        ( D ) OTHER INFORMATION: /note= "Xaa at position 10 is Ile,
            Met or Val; at position 11 is Glu, Leu, Val, Tyr
            or Ile; at position 12 is Trp, Tyr Val, Phe, Leu ( x i ) SEQUENCE DESCRIPTION: SEQ ID NO:1:

```
Leu  Xaa  Xaa  Ile  Xaa  Xaa  Xaa  Xaa  Lys  Xaa  Xaa  Xaa  Xaa
 1                  5                           10
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Xaa  Ile  Val  Xaa  Ala  Met  Lys  Met  Xaa
 1                  5
```

( 2 ) INFORMATION FOR SEQ ID NO:3:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Gly  Gln  Thr  Val  Leu  Val  Leu  Glu  Ala  Met  Lys  Met  Glu  Thr  Glu  Ile
```

( 2 ) INFORMATION FOR SEQ ID NO:4:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Asn Ala Pro Thr Asp Gly
                 20
```

```
Gly Glu Val Leu Leu Ile Leu Glu Ala Met Lys Met Glu Thr Glu Ile
1               5                   10                  15
Arg Ala Ala Gln Ala Gln
            20
```

( 2 ) INFORMATION FOR SEQ ID NO:5:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Gly Gln Cys Phe Ala Glu Ile Glu Val Met Lys Met Val Met Thr Leu
1               5                   10                  15
Thr Ala Gly Glu Ser Gly
            20
```

( 2 ) INFORMATION FOR SEQ ID NO:6:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Gly Asn Thr Leu Cys Ile Val Glu Ala Met Lys Met Met Asn Gln Ile
1               5                   10                  15
Glu Ala Asp Lys Ser Gly
            20
```

( 2 ) INFORMATION FOR SEQ ID NO:7:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Gly Gln Pro Val Ala Val Leu Ser Ala Met Lys Met Glu Met Ile Ile
1               5                   10                  15
Ser Ser Pro Ser Asp Gly
            20
```

( 2 ) INFORMATION FOR SEQ ID NO:8:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Gly Gln Pro Leu Cys Val Leu Ser Ala Met Lys Met Glu Thr Val Val
1               5                   10                  15
Thr Ser Pro Met Glu Gly
            20
```

( 2 ) INFORMATION FOR SEQ ID NO:9:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Gly Gln Pro Leu Val Leu Ser Ala Met Lys Met Glu Thr Val Val Thr
1               5                   10                  15
Ser Pro Val Thr Glu
        20
```

( 2 ) INFORMATION FOR SEQ ID NO:10:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Gly Ala Pro Leu Val Leu Ser Ala Met Lys Met Glu Thr Val Val Thr
1               5                   10                  15
Ala Pro Arg
```

( 2 ) INFORMATION FOR SEQ ID NO:11:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Gly Gln Glu Ile Cys Val Ile Glu Ala Met Lys Met Gln Asn Ser Met
1               5                   10                  15
Thr Ala Gly Lys Thr Gly
            20
```

( 2 ) INFORMATION FOR SEQ ID NO:12:

( i ) SEQUENCE CHARACTERISTICS:

(A) LENGTH: 22 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:12:

Gly Gln Pro Val Leu Val Leu Glu Ala Met Lys Met Glu His Val Val
1               5                   10                  15
Lys Ala Pro Ala Asn Gly
            20

(2) INFORMATION FOR SEQ ID NO:13:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:13:

Ala Met Lys Met
1

(2) INFORMATION FOR SEQ ID NO:14:

(i) SEQUENCE CHARACTERISTICS:
(A) LENGTH: 26 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:14:

Leu Glu Glu Val Asp Ser Thr Ser Ser Ala Ile Phe Asp Ala Met Lys
1               5                   10                  15
Met Val Trp Ile Ser Pro Thr Glu Phe Arg
            20                  25

(2) INFORMATION FOR SEQ ID NO:15:

(i) SEQUENCE CHARACTERISTICS:
(A) LENGTH: 27 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:15:

Gln Gly Asp Arg Asp Glu Thr Leu Pro Met Ile Leu Arg Ala Met Lys
1               5                   10                  15
Met Glu Val Tyr Asn Pro Gly Gly His Glu Lys
            20                  25

(2) INFORMATION FOR SEQ ID NO:16:

(i) SEQUENCE CHARACTERISTICS:
(A) LENGTH: 29 amino acids
(B) TYPE: amino acid
(C) STRANDEDNESS: single
(D) TOPOLOGY: linear (ii) MOLECULE TYPE: peptide ( x i ) SEQUENCE DESCRIPTION: SEQ ID NO:16:

Ser Lys Cys Ser Tyr Ser His Asp Leu Lys Ile Phe Glu Ala Gln Lys
1               5                   10                  15

Met Leu Val His Ser Tyr Leu Arg Val Met Tyr Asn Tyr
            20                  25

( 2 ) INFORMATION FOR SEQ ID NO:17:

( i ) SEQUENCE CHARACTERISTICS:
( A ) LENGTH: 22 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:17:

Met Ala Ser Ser Asp Asp Gly Leu Leu Thr Ile Phe Asp Ala Thr Lys
1               5                   10                  15

Met Met Phe Ile Arg Thr
            20

( 2 ) INFORMATION FOR SEQ ID NO:18:

( i ) SEQUENCE CHARACTERISTICS:
( A ) LENGTH: 27 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:18:

Ser Tyr Met Asp Arg Thr Asp Val Pro Thr Ile Leu Glu Ala Met Lys
1               5                   10                  15

Met Glu Leu His Thr Thr Pro Trp Ala Cys Arg
            20                  25

( 2 ) INFORMATION FOR SEQ ID NO:19:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:19:

Ser Phe Pro Pro Ser Leu Pro Asp Lys Asn Ile Phe Glu Ala Met Lys
1               5                   10                  15

Met Tyr Val Ile Thr
            20

( 2 ) INFORMATION FOR SEQ ID NO:20:

( i ) SEQUENCE CHARACTERISTICS:
( A ) LENGTH: 27 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:20:

Ser Val Val Pro Glu Pro Gly Trp Asp Gly Pro Phe Glu Ser Met Lys
1               5                   10                  15

```
            Met   Val   Tyr   His   Ser   Gly   Ala   Gln   Ser   Gly   Gln
                              20                            25
```

( 2 ) INFORMATION FOR SEQ ID NO:21:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

```
Val   Arg   His   Leu   Pro   Pro   Pro   Leu   Pro   Ala   Leu   Phe   Asp   Ala   Met   Lys
1                       5                             10                              15

Met   Glu   Phe   Val   Thr   Ser   Val   Gln   Phe
                  20                        25
```

( 2 ) INFORMATION FOR SEQ ID NO:22:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Asp   Met   Thr   Met   Pro   Thr   Gly   Met   Thr   Lys   Ile   Phe   Glu   Ala   Met   Lys
1                       5                             10                              15

Met   Glu   Val   Ser   Thr
                  20
```

( 2 ) INFORMATION FOR SEQ ID NO:23:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

```
Ala   Thr   Ala   Gly   Pro   Leu   His   Glu   Pro   Asp   Ile   Phe   Leu   Ala   Met   Lys
1                       5                             10                              15

Met   Glu   Val   Val   Asp   Val   Thr   Asn   Lys   Ala   Gly   Gln
                  20                        25
```

( 2 ) INFORMATION FOR SEQ ID NO:24:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

```
Ser   Met   Trp   Glu   Thr   Leu   Asn   Ala   Gln   Lys   Thr   Val   Leu   Leu
1                       5                             10
```

( 2 ) INFORMATION FOR SEQ ID NO:25:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:25:

Ser His Pro Ser Gln Leu Met Thr Asn Asp Ile Phe Glu Gly Met Lys
1               5                   10                  15

Met Leu Tyr His
            20

( 2 ) INFORMATION FOR SEQ ID NO:26:

( i ) SEQUENCE CHARACTERISTICS:
( A ) LENGTH: 26 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:26:

Ser Ile Glu Arg Gly Gly Ser Thr His Lys Ile Leu Ala Ala Met Lys
1               5                   10                  15

Met Tyr Gln Val Ser Thr Pro Ser Cys Ser
            20                  25

( 2 ) INFORMATION FOR SEQ ID NO:27:

( i ) SEQUENCE CHARACTERISTICS:
( A ) LENGTH: 23 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:27:

Thr Ser Glu Leu Ser Lys Leu Asp Ala Thr Ile Phe Ala Ala Met Lys
1               5                   10                  15

Met Gln Trp Trp Asn Pro Gly
            20

( 2 ) INFORMATION FOR SEQ ID NO:28:

( i ) SEQUENCE CHARACTERISTICS:
( A ) LENGTH: 22 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:28:

Val Met Glu Thr Gly Leu Asp Leu Arg Pro Ile Leu Thr Gly Met Lys
1               5                   10                  15

Met Asp Trp Ile Pro Lys
            20

( 2 ) INFORMATION FOR SEQ ID NO:29:

( i ) SEQUENCE CHARACTERISTICS:
( A ) LENGTH: 15 amino acids
( B ) TYPE: amino acid
( C ) STRANDEDNESS: single ( D ) TOPOLOGY: linear ( i i ) MOLECULE TYPE: peptide ( i x ) FEATURE:
    ( A ) NAME/KEY: Region
    ( B ) LOCATION: one-of(1, 2, 3, 11, 12, 13, 14, 15)
    ( D ) OTHER INFORMATION: /note= "Xaa is any amino acid coded for by the NNK codon."

( x i ) SEQUENCE DESCRIPTION: SEQ ID NO:29:

Xaa Xaa Xaa Ile Phe Glu Ala Met Lys Met Xaa Xaa Xaa Xaa Xaa
1               5                   10                  15

( 2 ) INFORMATION FOR SEQ ID NO:30:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:30:

Leu His His Ile Leu Asp Ala Gln Lys Met Val Trp Asn His Arg
1               5                   10                  15

( 2 ) INFORMATION FOR SEQ ID NO:31:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:31:

Pro Gln Gly Ile Phe Glu Ala Gln Lys Met Leu Trp Arg Ser
1               5                   10

( 2 ) INFORMATION FOR SEQ ID NO:32:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:32:

Leu Ala Gly Thr Phe Glu Ala Leu Lys Met Ala Trp His Glu His
1               5                   10                  15

( 2 ) INFORMATION FOR SEQ ID NO:33:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:33:

Leu Asn Ala Ile Phe Glu Ala Met Lys Met Glu Tyr Ser Gly
1               5                   10

( 2 ) INFORMATION FOR SEQ ID NO:34:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:34:

```
Leu  Gly  Gly  Ile  Phe  Glu  Ala  Met  Lys  Met  Glu  Leu  Arg  Asp
1                  5                        10
```

( 2 ) INFORMATION FOR SEQ ID NO:35:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:35:

```
Leu  Leu  Arg  Thr  Phe  Glu  Ala  Met  Lys  Met  Asp  Trp  Arg  Asn  Gly
1                  5                        10                        15
```

( 2 ) INFORMATION FOR SEQ ID NO:36:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:36:

```
Leu  Ser  Thr  Ile  Met  Glu  Gly  Met  Lys  Met  Tyr  Ile  Gln  Arg  Ser
1                  5                        10                        15
```

( 2 ) INFORMATION FOR SEQ ID NO:37:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:37:

```
Leu  Ser  Asp  Ile  Phe  Glu  Ala  Met  Lys  Met  Val  Tyr  Arg  Pro  Cys
1                  5                        10                        15
```

( 2 ) INFORMATION FOR SEQ ID NO:38:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:38:

```
Leu  Glu  Ser  Met  Leu  Glu  Ala  Met  Lys  Met  Gln  Trp  Asn  Pro  Gln
1                  5                        10                        15
```

( 2 ) INFORMATION FOR SEQ ID NO:39:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

```
Leu Ser Asp Ile Phe Asp Ala Met Lys Met Val Tyr Arg Pro Gln
 1               5                  10                  15
```

( 2 ) INFORMATION FOR SEQ ID NO:40:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:40:

```
Leu Ala Pro Phe Phe Glu Ser Met Lys Met Val Trp Arg Glu His
 1               5                  10                  15
```

( 2 ) INFORMATION FOR SEQ ID NO:41:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:41:

```
Leu Lys Gly Ile Phe Glu Ala Met Lys Met Glu Tyr Thr Ala Met
 1               5                  10                  15
```

( 2 ) INFORMATION FOR SEQ ID NO:42:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:42:

```
Leu Glu Gly Ile Phe Glu Ala Met Lys Met Glu Tyr Ser Asn Ser
 1               5                  10                  15
```

( 2 ) INFORMATION FOR SEQ ID NO:43:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:43:

```
Leu Leu Gln Thr Phe Asp Ala Met Lys Met Glu Trp Leu Pro Lys
 1               5                  10                  15
```

( 2 ) INFORMATION FOR SEQ ID NO:44:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:44:

```
Val Phe Asp Ile Leu Glu Ala Gln Lys Val Val Thr Leu Arg Phe
 1               5                  10                  15
```

( 2 ) INFORMATION FOR SEQ ID NO:45:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:45:

```
Leu Val Ser Met Phe Asp Gly Met Lys Met Glu Trp Lys Thr Leu
 1               5                  10                  15
```

( 2 ) INFORMATION FOR SEQ ID NO:46:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:46:

```
Leu Glu Pro Ile Phe Glu Ala Met Lys Met Asp Trp Arg Leu Glu
 1               5                  10                  15
```

( 2 ) INFORMATION FOR SEQ ID NO:47:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:47:

```
Leu Lys Glu Ile Phe Glu Gly Met Lys Met Glu Phe Val Lys Pro
 1               5                  10                  15
```

( 2 ) INFORMATION FOR SEQ ID NO:48:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:48:

```
Leu Gly Gly Ile Glu Ala Gln Lys Met Leu Leu Tyr Arg Gly Asn
 1               5                  10                  15
```

( 2 ) INFORMATION FOR SEQ ID NO:49:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: one-of(1, 2, 3, 4, 5, 6, 14, 15, 16, 17, 18)
    ( D ) OTHER INFORMATION: /note= "Xaa is any amino acid coded for
          by the NNK codon."

( x i ) SEQUENCE DESCRIPTION: SEQ ID NO:49:

Xaa Xaa Xaa Xaa Xaa Xaa Ile Phe Glu Ala Met Lys Met Xaa Xaa Xaa
1               5                   10                  15
Xaa Xaa ( 2 ) INFORMATION FOR SEQ ID NO:50:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:50:

Arg Pro Val Leu Glu Asn Ile Phe Glu Ala Met Lys Met Glu Val Trp
1               5                   10                  15
Lys Pro ( 2 ) INFORMATION FOR SEQ ID NO:51:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:51:

Arg Ser Pro Ile Ala Glu Ile Phe Glu Ala Met Lys Met Glu Tyr Arg
1               5                   10                  15
Glu Thr ( 2 ) INFORMATION FOR SEQ ID NO:52:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:52:

Gln Asp Ser Ile Met Pro Ile Phe Glu Ala Met Lys Met Ser Trp His
1               5                   10                  15
Val Asn ( 2 ) INFORMATION FOR SEQ ID NO:53:

(i) SEQUENCE CHARACTERISTICS:
  (A) LENGTH: 18 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:53:

```
Asp Gly Val Leu Phe Pro Ile Phe Glu Ala Met Lys Met Ile Arg Leu
1               5                   10                  15
Glu Thr
```

(2) INFORMATION FOR SEQ ID NO:54:

(i) SEQUENCE CHARACTERISTICS:
    (A) LENGTH: 18 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:54:

```
Val Ser Arg Thr Met Thr Asn Phe Glu Ala Met Lys Met Ile Tyr His
1               5                   10                  15
Asp Leu
```

(2) INFORMATION FOR SEQ ID NO:55:

(i) SEQUENCE CHARACTERISTICS:
    (A) LENGTH: 17 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:55:

```
Asp Val Leu Leu Pro Thr Val Phe Glu Ala Met Lys Met Tyr Ile Thr
1               5                   10                  15
Lys
```

(2) INFORMATION FOR SEQ ID NO:56:

(i) SEQUENCE CHARACTERISTICS:
    (A) LENGTH: 18 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:56:

```
Pro Asn Asp Leu Glu Arg Ile Phe Asp Ala Met Lys Ile Val Thr Val
1               5                   10                  15
His Ser
```

(2) INFORMATION FOR SEQ ID NO:57:

(i) SEQUENCE CHARACTERISTICS:
    (A) LENGTH: 18 amino acids
    (B) TYPE: amino acid
    (C) STRANDEDNESS: single
    (D) TOPOLOGY: linear (ii) MOLECULE TYPE: peptide ( x i ) SEQUENCE DESCRIPTION: SEQ ID NO:57:

Thr Arg Ala Leu Leu Glu Ile Phe Asp Ala Gln Lys Met Leu Tyr Gln
1               5                   10                  15

His Leu ( 2 ) INFORMATION FOR SEQ ID NO:58:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:58:

Arg Asp Val His Val Gly Ile Phe Glu Ala Met Lys Met Tyr Thr Val
1               5                   10                  15

Glu Thr ( 2 ) INFORMATION FOR SEQ ID NO:59:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:59:

Gly Asp Lys Leu Thr Glu Ile Phe Glu Ala Met Lys Ile Gln Trp Thr
1               5                   10                  15

Ser Gly ( 2 ) INFORMATION FOR SEQ ID NO:60:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:60:

Leu Glu Gly Leu Arg Ala Val Phe Glu Ser Met Lys Met Glu Leu Ala
1               5                   10                  15

Asp Glu ( 2 ) INFORMATION FOR SEQ ID NO:61:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:61:

Val Ala Asp Ser His Asp Thr Phe Ala Ala Met Lys Met Val Trp Leu
1               5                   10                  15

Asp Thr ( 2 ) INFORMATION FOR SEQ ID NO:62:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:62:

```
Gly Leu Pro Leu Gln Asp Ile Leu Glu Ser Met Lys Ile Val Met Thr
  1               5                  10                  15

Ser Gly
```

( 2 ) INFORMATION FOR SEQ ID NO:63:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:63:

```
Arg Val Pro Leu Glu Ala Ile Phe Glu Gly Ala Lys Met Ile Trp Val
  1               5                  10                  15

Pro Asn Asn
```

( 2 ) INFORMATION FOR SEQ ID NO:64:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:64:

```
Pro Met Ile Ser His Lys Asn Phe Glu Ala Met lys Met Lys Phe Val
  1               5                  10                  15

Pro Glu
```

( 2 ) INFORMATION FOR SEQ ID NO:65:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:65:

```
Lys Leu Gly Leu Pro Ala Met Phe Glu Ala Met Lys Met Glu Trp His
  1               5                  10                  15

Pro Ser
```

( 2 ) INFORMATION FOR SEQ ID NO:66:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:66:

Gln Pro Ser Leu Leu Ser Ile Phe Glu Ala Met Lys Met Gln Ala Ser
1               5                   10                  15

Leu Met ( 2 ) INFORMATION FOR SEQ ID NO:67:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:67:

Leu Leu Glu Leu Arg Ser Asn Phe Glu Ala Met Lys Met Glu Trp Gln
1               5                   10                  15

Ile Ser ( 2 ) INFORMATION FOR SEQ ID NO:68:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:68:

Asp Glu Glu Leu Asn Gln Ile Phe Glu Ala Met Lys Met Tyr Pro Leu
1               5                   10                  15

Val His Val Thr Lys
                20

( 2 ) INFORMATION FOR SEQ ID NO:69:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(1..10, 12..21)
        ( D ) OTHER INFORMATION: /note= "Xaa is any amino acid coded for
            by the NNK codon."

( x i ) SEQUENCE DESCRIPTION: SEQ ID NO:69:

Xaa Xaa Xaa Xaa Xaa Xaa Xaa Xaa Xaa Xaa Lys Xaa Xaa Xaa Xaa Xaa
1               5                   10                  15

Xaa Xaa Xaa Xaa Xaa
                20

( 2 ) INFORMATION FOR SEQ ID NO:70:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:70:

Ser Asn Leu Val Ser Leu Leu His Ser Gln Lys Ile Leu Trp Thr Asp
1               5                   10                  15

Pro Gln Ser Phe Gly
            20

( 2 ) INFORMATION FOR SEQ ID NO:71:

( i ) SEQUENCE CHARACTERISTICS:
          ( A ) LENGTH: 21 amino acids
          ( B ) TYPE: amino acid
          ( C ) STRANDEDNESS: single
          ( D ) TOPOLOGY: linear ( i i ) MOLECULE TYPE: peptide ( x i ) SEQUENCE DESCRIPTION: SEQ ID NO:71:

Leu Phe Leu His Asp Phe Leu Asn Ala Gln Lys Val Glu Leu Tyr Pro
1               5                   10                  15

Val Thr Ser Ser Gly
            20

( 2 ) INFORMATION FOR SEQ ID NO:72:

( i ) SEQUENCE CHARACTERISTICS:
          ( A ) LENGTH: 16 amino acids
          ( B ) TYPE: amino acid
          ( C ) STRANDEDNESS: single
          ( D ) TOPOLOGY: linear ( i i ) MOLECULE TYPE: peptide ( x i ) SEQUENCE DESCRIPTION: SEQ ID NO:72:

Ser Asp Ile Asn Ala Leu Leu Ser Thr Gln Lys Ile Tyr Trp Ala His
1               5                   10                  15

( 2 ) INFORMATION FOR SEQ ID NO:73:

( i ) SEQUENCE CHARACTERISTICS:
          ( A ) LENGTH: 23 amino acids
          ( B ) TYPE: amino acid
          ( C ) STRANDEDNESS: single
          ( D ) TOPOLOGY: linear ( i i ) MOLECULE TYPE: peptide ( i x ) FEATURE:
          ( A ) NAME/KEY: Modified-site
          ( B ) LOCATION: one-of(3, 4, 6, 7, 18, 19, 20)
          ( D ) OTHER INFORMATION: /note= "Xaa is any amino acid coded for
                 by the NNK codon."

( i x ) FEATURE:
          ( A ) NAME/KEY: Modified-site
          ( B ) LOCATION: one-of(9, 10, 14, 17)
          ( D ) OTHER INFORMATION: /note= "Xaa at position 9 is Phe or
                 Leu; at position 10 is Glu or Asp; at position 14
                 is Met or Ile; at position 17 is His or Arg."

( x i ) SEQUENCE DESCRIPTION: SEQ ID NO:73:

Met Ala Xaa Xaa Leu Xaa Xaa Ile Xaa Xaa Ala Gln Lys Xaa Glu Trp
1               5                   10                  15

Xaa Xaa Xaa Xaa Gly Gly Ser
            20

( 2 ) INFORMATION FOR SEQ ID NO:74:

( i ) SEQUENCE CHARACTERISTICS:
   ( A ) LENGTH: 23 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:74:

Met Ala Ser Ser Leu Arg Gln Ile Leu Asp Ser Gln Lys Met Glu Trp
1               5                   10                  15

Arg Ser Asn Ala Gly Gly Ser
                20

( 2 ) INFORMATION FOR SEQ ID NO:75:

( i ) SEQUENCE CHARACTERISTICS:
      ( A ) LENGTH: 23 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:75:

Met Ala His Ser Leu Val Pro Ile Phe Asp Ala Gln Lys Ile Glu Trp
1               5                   10                  15

Arg Asp Pro Phe Gly Gly Ser
                20

( 2 ) INFORMATION FOR SEQ ID NO:76:

( i ) SEQUENCE CHARACTERISTICS:
      ( A ) LENGTH: 23 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:76:

Met Gly Pro Asp Leu Val Asn Ile Phe Glu Ala Gln Lys Ile Glu Trp
1               5                   10                  15

His Pro Leu Thr Gly Gly Ser
                20

( 2 ) INFORMATION FOR SEQ ID NO:77:

( i ) SEQUENCE CHARACTERISTICS:
      ( A ) LENGTH: 23 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:77:

Met Ala Phe Ser Leu Arg Ser Ile Leu Glu Ala Gln Lys Met Glu Leu
1               5                   10                  15

Arg Asn Thr Pro Gly Gly Ser
                20

( 2 ) INFORMATION FOR SEQ ID NO:78:

( i ) SEQUENCE CHARACTERISTICS:
      ( A ) LENGTH: 23 amino acids
      ( B ) TYPE: amino acid
      ( C ) STRANDEDNESS: single ( D ) TOPOLOGY: linear ( i i ) MOLECULE TYPE: peptide ( x i ) SEQUENCE DESCRIPTION: SEQ ID NO:78:

Met Ala Gly Gly Leu Asn Asp Ile Phe Glu Ala Gln Lys Ile Glu Trp
1               5                   10                  15

His Glu Asp Thr Gly Gly Ser
            20

( 2 ) INFORMATION FOR SEQ ID NO:79:

( i ) SEQUENCE CHARACTERISTICS:
       ( A ) LENGTH: 23 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:79:

Met Ser Ser Tyr Leu Ala Pro Ile Phe Glu Ala Gln Lys Ile Glu Trp
1               5                   10                  15

His Ser Ala Tyr Gly Gly Ser
            20

( 2 ) INFORMATION FOR SEQ ID NO:80:

( i ) SEQUENCE CHARACTERISTICS:
       ( A ) LENGTH: 23 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:80:

Met Ala Lys Ala Leu Gln Lys Ile Leu Glu Ala Gln Lys Met Glu Trp
1               5                   10                  15

Arg Ser His Pro Gly Gly Ser
            20

( 2 ) INFORMATION FOR SEQ ID NO:81:

( i ) SEQUENCE CHARACTERISTICS:
       ( A ) LENGTH: 23 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:81:

Met Ala Phe Gln Leu Cys Lys Ile Phe Tyr Ala Gln Lys Met Glu Trp
1               5                   10                  15

His Gly Val Gly Gly Gly Ser
            20

( 2 ) INFORMATION FOR SEQ ID NO:82:

( i ) SEQUENCE CHARACTERISTICS:
       ( A ) LENGTH: 23 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:82:

Met Ala Gly Ser Leu Ser Thr Ile Phe Asp Ala Gln Lys Ile Glu Trp
1               5                   10                  15

His Val Gly Lys Gly Gly Ser
            20

( 2 ) INFORMATION FOR SEQ ID NO:83:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:83:

Met Ala Gln Gln Leu Pro Asp Ile Phe Asp Ala Gln Lys Ile Glu Trp
1               5                   10                  15

Arg Ile Ala Gly Gly Gly Ser
            20

( 2 ) INFORMATION FOR SEQ ID NO:84:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:84:

Met Ala Gln Arg Leu Phe His Ile Leu Asp Ala Gln Lys Ile Glu Trp
1               5                   10                  15

His Gly Pro Lys Gly Gly Ser
            20

( 2 ) INFORMATION FOR SEQ ID NO:85:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:85:

Met Ala Gly Cys Leu Gly Pro Ile Phe Glu Ala Gln Lys Met Glu Trp
1               5                   10                  15

Arg His Phe Val Gly Gly Ser
            20

( 2 ) INFORMATION FOR SEQ ID NO:86:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:86:

Met Ala Trp Ser Leu Lys Pro Ile Phe Asp Ala Gln Lys Ile Glu Trp
1               5                   10                  15

```
        His   Ser   Pro   Gly   Gly   Gly   Ser
                          20
```

( 2 ) INFORMATION FOR SEQ ID NO:87:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:87:

```
  Met   Ala   Leu   Gly   Leu   Thr   Arg   Ile   Leu   Asp   Ala   Gln   Lys   Ile   Glu   Trp
  1                       5                             10                            15
  His   Arg   Asp   Ser   Gly   Gly   Ser
                          20
```

( 2 ) INFORMATION FOR SEQ ID NO:88:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:88:

```
  Met   Ala   Gly   Ser   Leu   Arg   Gln   Ile   Leu   Asp   Ala   Gln   Lys   Ile   Glu   Trp
  1                       5                             10                            15
  Arg   Arg   Pro   Leu   Gly   Gly   Ser
                          20
```

( 2 ) INFORMATION FOR SEQ ID NO:89:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:89:

```
  Met   Ala   Asp   Arg   Leu   Ala   Tyr   Ile   Leu   Glu   Ala   Gln   Lys   Met   Glu   Trp
  1                       5                             10                            15
  His   Pro   His   Lys   Gly   Gly   Ser
                          20
```

( 2 ) INFORMATION FOR SEQ ID NO:90:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:90:

```
  Val   Val   His   Gly   Glu   Gln   Val   Gly   Gly   Glu   Ala   Ser   Gly   Gly   Gly
  1                       5                             10                            15
```

( 2 ) INFORMATION FOR SEQ ID NO:91:

( i ) SEQUENCE CHARACTERISTICS:
  ( A ) LENGTH: 103 base pairs
  ( B ) TYPE: nucleic acid
  ( C ) STRANDEDNESS: single
  ( D ) TOPOLOGY: linear ( i i ) MOLECULE TYPE: DNA (oligonucleotide)

( x i ) SEQUENCE DESCRIPTION: SEQ ID NO:91:

```
GAGGTGGTNN KNNKNNKNNK NNKNNKNNKN NKNNKNNKAT CGTTNNKGCT ATGAAAATGN        60
NKNNKNNKNN KNNKNNKNNK NNKNNKNNKT AACTAAGTAA AGC                         103
```

( 2 ) INFORMATION FOR SEQ ID NO:92:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:92:

```
ACCACCTCCG G                                                             11
```

( 2 ) INFORMATION FOR SEQ ID NO:93:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:93:

```
TTACTTAGTT A                                                             11
```

( 2 ) INFORMATION FOR SEQ ID NO:94:

( i ) SEQUENCE CHARACTERISTICS:
    ( A ) LENGTH: 67 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:94:

```
GAGGTGGTNN KNNKNNKATC TTTGAAGCTA TGAAAATGNN KNNKNNKNNK NNKTAACTAA        60
GTAAAGC                                                                  67
```

( 2 ) INFORMATION FOR SEQ ID NO:95:

( i ) SEQUENCE CHARACTERISTICS:
    ( A ) LENGTH: 76 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:95:

```
GAGGTGGTNN KNNKNNKNNK NNKNNKATCT TGAAGCTAT GAAAATGNNK NNKNNKNNKN         60
NKTAACTAAG TAAAGC                                                        76
```

( 2 ) INFORMATION FOR SEQ ID NO:96:

( i ) SEQUENCE CHARACTERISTICS:
  ( A ) LENGTH: 85 base pairs
  ( B ) TYPE: nucleic acid
  ( C ) STRANDEDNESS: single
  ( D ) TOPOLOGY: linear ( i i ) MOLECULE TYPE: DNA (oligonucleotide)

( x i ) SEQUENCE DESCRIPTION: SEQ ID NO:96:

GAGGTGGTNN KNNKNNKNNK NNKNNKNNKN NKNNKNNKAA ANNKNNKNNK NNKNNKNNKN    60

NKNNKNNKNN KTAACTAAGT AAAGC    85

( 2 ) INFORMATION FOR SEQ ID NO:97:

( i ) SEQUENCE CHARACTERISTICS:
    ( A ) LENGTH: 96 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:97:

CTAGCTAACT AATGGAGGAT ACATAAATGG CTNNKNNKCT GNNKNVKATT TTNGANGCTC    60

ARAAAATNGA ATGGCRYNNK NNKNNKGGTG GTAGCC    96

( 2 ) INFORMATION FOR SEQ ID NO:98:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:98:

TCCTCCATTA GTTAG    15

( 2 ) INFORMATION FOR SEQ ID NO:99:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:99:

TCGAGGCTAC CACC    14

( 2 ) INFORMATION FOR SEQ ID NO:100:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:100:

GAATTCAATT GTGAGCGCTC ACAATTGAAT TC    32

( 2 ) INFORMATION FOR SEQ ID NO:101:

(i) SEQUENCE CHARACTERISTICS:
    (A) LENGTH: 57 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:101:

TACAGTGCTA GCTAACTAAT GGAGGATACA TAAATGAAGG ATAACACCGT GCCACTG    57

(2) INFORMATION FOR SEQ ID NO:102:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:102:

GTATCAGAGC TCTTATTTT CTGCACTACG CAGGGA    36

BIOTINYLATION OF PROTEINS

CROSS-REFERENCE TO RELATED APPLICATION

This application is a continuation-in-part application of U.S. patent application Ser. No. 08/099,991, filed Jul. 30, 1993, now abandoned, which is hereby incorporated by reference and benefit is claimed of its filing data.

FIELD OF THE INVENTION

The present invention relates to methods for producing biotinylated proteins in vitro and in recombinant host cells. The invention therefore relates to the field of molecular biology, but given the diverse uses for recombinant proteins, the invention also relates to the fields of chemistry, pharmacology, biotechnology, and medical diagnostics.

DESCRIPTION OF THE BACKGROUND ART

The ability to synthesize DNA chemically has made possible the construction of peptides and proteins not otherwise found in nature and useful in a wide variety of methods that would otherwise be very difficult or impossible to perform. One illustrative example of this technology relates to the class of molecules known as receptors. Receptor proteins mediate important biological functions through interactions with ligands. For many years, researchers have attempted to isolate and identify ligands that interact with receptors in ways that can help ameliorate human (and other) disease. The advent of molecular biology has revolutionized the way these researchers study receptor-ligand interaction. For instance, standard molecular biology techniques have enabled the cloning and high-level expression of many receptors in recombinant host cells.

The patent literature, for instance, is replete with publications describing the recombinant expression of receptor proteins. See, e.g., PCT Patent Pub. No. 91/18982 and U.S. Pat. Nos. 5,081,228 and 4,968,607, which describe recombinant DNA molecules encoding the IL-1 receptor; U.S. Pat. Nos. 4,816,565; 4,578,335; and 4,845,198, which describe recombinant DNA and proteins relating to the IL-2 receptor; PCT Patent Pub. No. 91/08214, which describes EGF receptor gene related nucleic acids; PCT Patent Pub. No. 91/16431 and U.S. Pat. No. 4,897,264, which describe the interferon gamma receptor and related proteins and nucleic acids; European Patent Office (EPO) Pub. No. 377,489, which describes the C5a receptor protein; PCT Patent Pub. No. 90/08822, which describes the EPO receptor and related nucleic acids; and PCT Patent Pub. No. 92/01715, which describes MHC receptors.

Several of the above publications not only describe how to isolate a particular receptor protein (or the gene encoding the protein) but also describe variants of the receptor that may be useful in ways the natural or native receptor is not. For instance, PCT Patent Pub. No. 91/16431 describes soluble versions of the gamma interferon receptor, while PCT Patent Pub. No. 92/01715 describes how to produce soluble cell-surface dimeric proteins. This later technology involves expression of the receptor with a signal for lipid attachment; once the lipid is attached to the receptor, the receptor becomes anchored in the cell membrane, where the dimeric form of the receptor is assembled. See also U.S. patent application Ser. No. 947,339, filed on Sep. 18, 1992, and incorporated herein by reference for all purposes, which describes how HPAP-containing receptors can be cleaved from the cell surface and how the anchoring sequences that remain can serve as recognition sequences for antibodies that are used to immobilize the receptor.

The advances made with respect to receptor cloning and expression have been accompanied by advances in technology relating to methods for screening a receptor against compounds that may interact with the receptor in a desired fashion. One such advance relates to the generation of large numbers of compounds, or potential ligands, in a variety of random and semi-random "peptide diversity" generation systems. These systems include the "peptides on plasmids" system described in U.S. Pat. No. 5,338,665, which is a continuation-in-part of U.S. Pat. No. 5,270,170; the "peptides on phage" system described in U.S. patent application Ser. No. 718,577, filed Jun. 20, 1991, which is a continuation-in-part of Ser. No. 541,108, filed Jun. 20, 1990; Cwirla et al., August 1990, Proc. Natl. Acad. Sci. USA 87: 6378–6382; Barrett et al., 1992, Analyt. Biochem. 204: 357–364; and PCT Patent Pub. Nos. 91/18980 and 91/19818; the phage-based antibody display systems described in U.S. patent application Ser. No. 517,659, filed May 11, 1990, and PCT Patent Pub. No. 91/17271; the bead-based systems for generating and screening nucleic acid ligands described in PCT Pub. Nos. 91/19813, 92/05258, and 92/14843; the bead-based system described in U.S. patent application Ser. No. 946,239, filed Sep. 16, 1992, which is a continuation-in-part of Ser. No. 762,522, filed Sep. 18, 1991; and the "very large scaled immobilized polymer synthesis" system described in U.S. Pat. No. 5,143,854; PCT Patent Pub. Nos. 90/15070 and 92/10092, U.S. patent application Ser. No. 624,120, filed Dec. 6, 1990; Fodor et al., Feb. 15, 1991, Science 251: 767–773; Dower and Fodor, 1991, Ann. Rep. Med. Chem. 26:271–180; and U.S. patent application Ser. No. 805,727, filed Dec. 6, 1991. Each of the above references is incorporated herein by reference for all purposes.

Other developments relate to how the receptor is used in such screening methods. One important advance relates to the development of reagents and methods for immobilizing one or more receptors in a spatially defined array, as described in PCT Patent Pub. No. 91.07087. In one embodiment of this method, a receptor is attached to avidin and then immobilized on a surface that bears biotin groups. The surface is first prepared, however, with caged biotin groups, which will not bind avidin until the caging group is removed by, in this embodiment, irradiation. Once the avidinylated receptor is bound to the biotin groups on the surface, the surface can be used in screening compounds against the receptor.

Biotin is a coenzyme that is covalently attached to several enzymes involved in the transfer of activated carboxyl groups. As the above example illustrates, biotin labeling of molecules not normally biotinylated can be used to label, detect, purify, and/or immobilize such molecules. These methods also rely upon the proteins avidin and streptavidin, which bind very tightly and specifically to biotin and other biotin-binding molecules, some of which bind to biotin with different affinity than avidin. Typically, the biotinylated molecules used in such methods are prepared by an in vitro biotinylation process. A method for biotinylating proteins synthesized by recombinant DNA techniques in vivo would eliminate the need to biotinylate these proteins chemically after purification and would greatly simplify the purification process, due to the ability to use the biotin as an affinity tag (see Green, 1975, Adv. Protein Res. 29:85–133, incorporated herein by reference).

Biotin is added to proteins in vivo through the formation of an amide bond between the biotin carboxyl group and the epsilon-amino group of specific lysine residues in a reaction that requires ATP. In normal *E. coli*, only one protein is biotinylated, the biotin carboxyl carrier protein (BCCP) subunit of acetyl-CoA carboxylase. This reaction is catalyzed by the biotin-protein ligase (BirA), the product of the birA gene (see Cronan, 1989, *Cell* 58: 427-429, incorporated herein by reference).

Others have proposed a means by which blown labeling can be accomplished in vivo by the addition of a domain of at least 75 amino acids to recombinant proteins (see Cronan, 1990, *J. Biol. Chem.* 265: 10327–10333, incorporated herein by reference). See also Cress et al., 1993, *Promega Notes* 42: 2–7. Addition of this 75 amino acid domain to several different proteins leads to the biotinylation of the fusion proteins by BirA on a specific lysine of the added domain. Addition of smaller fragments of the 75 residue domain does not lead to biotinylation, implying that a reasonably complex recognition domain is required. Changes in the sequence of biotinylated proteins as far as 33 residues from the modified lysine abolish biotinylation (see Murtif and Samols, 1987, *J. Biol. Chem.* 262: 11813–11816). Changes close to the lysine also affect biotinylation (see Shenoy et al., 1988, *FASEB J.* 2: 2505–2511, and Shenoy et al., 1992, *J. Biol. Chem.* 267: 18407–18412). Unfortunately, however, the addition of such a large protein domain may negatively affect the biochemical properties of a biolinylated protein. Smaller domains that specify biotinylation would be very beneficial, in that such domains would have a minimal structural effect on the wide variety of possible fusion partners. Also, the 75 residue domain does not lead to complete biotinylation of the domain, and improved domains could be more efficient. The present invention provides such improved biotinylation domains.

SUMMARY OF THE INVENTION

The present invention provides useful compounds, reagents, methods, and kits for biotinylating proteins. In a first aspect, the present invention provides a method for biotinylating a protein, said method comprising: (a) constructing a recombinant DNA expression vector that encodes a fusion protein comprising said protein and a biotinylation peptide less than about 50 amino acids in length; (b) transforming a recombinant host cell capable of synthesizing a biotinylation enzyme with said vector; and (c) culturing said host cell under conditions in which biotin is present and such that said fusion protein and biotinylation enzyme are expressed, resulting in biotinylation of said fusion protein. If the host cell does not naturally produce biotin, then one can add biotin to the media. In a preferred embodiment, the host cell is *E. coli*, and the biotinylation enzyme is BirA.

Thus, in the preferred embodiment, a biotinylation peptide of the present invention can be added to any protein expressed in *E. coli* with a sufficient time of retention in the cytoplasm to permit BirA to act. If high expression levels of biotinylated protein are desired, then one can readily overexpress the BirA protein at the same time (see Buoncristiani et al., 1988, *J. Biol. Chem.* 263, 1013–1016, incorporated herein by reference). In similar fashion, host cells that lack an endogenous biotin protein ligase (called a biotinylation enzyme) can be transformed with a vector that codes for expression of the birA gene to provide or enhance their ability to biotinylate recombinant proteins. Where, due to the conservation of the recognition domains, the endogenous biotin-protein ligase of other non-*E. coli* cell types recognize the novel biotinylation sequences, no such recombinant expression of a biotinylation enzyme is required. One can also perform the biotinylation reaction in vitro using a biotinylation enzyme such as purified BirA (see Buoncristiani, supra), biotin, and biotinylation sequence peptide-tagged proteins, which proteins may be either produced in recombinant host cells or by in vitro translation. One can also use biotin analogues, such as 2-iminobiotin, which has a lower affinity for avidin than biotin and so may be preferred for some applications, in place of biotin, in like method.

The present invention also provides reagents useful in the present method, including peptides, proteins, oligonucleotides, and recombinant DNA expression vectors. Thus, the present invention provides biotinylated peptides less than 50 amino acids in length, typically 10 to 20 or more amino acids in length, and oligonucleotides comprising coding sequences for such peptides. In addition, the invention provides recombinant biotinylated proteins and expression vectors encoding those proteins. In a preferred embodiment the present biotinylation peptide is 13 amino acids long and is defined by Leu Xaa$_1$ Xaa$_2$ Ile Xaa$_3$ Xaa$_4$ Xaa$_5$ Xaa$_6$ Lys Xaa$_7$ Xaa$_8$ Xaa$_9$ Xaa$_{10}$ (SEQ. ID NO:1), where Xaa$_1$ is any amino acid, Xaa$_2$ is any amino acid other than large hydrophobic amino acids (such as Leu, Val, Ile, Trp, Phe, Tyr); Xaa$_3$ is Phe or Leu, Xaa$_4$ is Glu or Asp; Xaa$_5$ is Ala, Gly, Ser, or Thr; Xaa$_6$ is Gln or Met; Xa$_7$ is Ile, Met, or Val; Xaa$_8$ is Glu, Leu, Val, Tyr, or Ile; Xaa$_9$ is Trp, Tyr, Val, Phe, Leu, or Ile; and Xaa$_{10}$ is preferably Arg or His but may be any amino acid other than acidic amino acids such as Asp or Glu.

In summary, this invention provides a simple and efficient means to biotinylate recombinant proteins, providing for rapid purification, mobilization, labeling, and detection of those proteins. The method is useful for a variety of purposes and is widely commercially useful for research and diagnostic applications.

DESCRIPTION OF THE PREFERRED EMBODIMENT

I. Definitions

For purposes of understanding the present invention, the following terms are defined.

Amino acid residues in peptides are abbreviated as follows: Phenylalanine is Phe or F; Leucine is Leu or L; Isoleucine is Ile or I; Methionine is Met or M; Valine is Val or V; Serine is Set or S; Proline is Pro or P; Threonine is Thr or T; Alanine is Ala or A; Tyrosine is Tyr or Y; Histidine B, His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

The term "antibody" refers to antibodies and antibody fragments that retain the ability to bind the epitope that the intact antibody binds, whether the antibody or fragment is produced by hybridoma cell lines, by immunization to elicit a polyclonal antibody response, or by recombinant host cells that have been transformed with a recombinant DNA expression vector that encodes the antibody or antibody fragment.

The term "antigen" is defined as a molecule that induces the formation of an antibody or is capable of binding specifically to the antigen-binding sites of an antibody.

The term "biotinylation peptide" refers to an amino acid sequence which provides a biotinylatable sequence motif. Thus, a biotinylation peptide is peptide that is capable of being biotinylated.

The term "biotinylation enzyme" refers to the class of enzymes known as biotin protein ligases, or enzymes which biotinylate other proteins or peptides.

The term "effective amount" refers to an amount sufficient to induce a desired result.

The term "epitope" refers to that portion of an antigen that interacts with an antibody.

The term "fusion protein" generally refers to a protein which is a composite of two separate proteins which are normally not fused together as a single protein. Fusion proteins may be prepared by recombinant nucleic acid methods, i.e., as a result of transcription and translation of a gene fusion comprising a segment which encodes a biotinylation peptide and a segment which encodes one or more heterologous proteins, or by chemical synthesis methods well known in the art.

The term "host cell" refers to a eukaryotic or procaryotic cell or group of cells that can be or has been transformed by a recombinant DNA vector. For purposes of the present invention, procaryotic host cells are preferred.

The term "ligand" refers to a molecule that is recognized by a particular receptor. The agent bound by or reacting with a receptor is called a "ligand," a term which is definitionally meaningful primarily in terms of its counterpart receptor. The term "ligand" does not imply any particular molecular size or other structural or compositional feature other than that the substance in question is capable of binding or otherwise interacting with the receptor. A "ligand" may serve either as the natural ligand to which the receptor binds or as a functional analogue that may act as an agonist or antagonist. Examples of ligands that can be investigated with the present invention include, but are not restricted to, peptides and proteins such as agonists and antagonists for cell membrane receptors, toxins and venoms, epitopes such as viral epitopes, antibodies, hormones, enzyme substrates, and proteins.

The term "linker" or "spacer" refers to a molecule or group of molecules (such as a monomer or polymer) that connects two molecules and often serves to place the two molecules in a preferred configuration, e.g., so that a ligand can bind to a receptor with minimal steric hindrance.

The term "monomer" refers to any member of the set of molecules that can be joined together to form an oligomer or polymer. The set of monomers useful in the present invention includes, but is not restricted to, for the example of peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either sub unit alone.

The term "oligomer" or "polymer" refers to the compounds formed by the chemical or enzymatic addition of two or more monomers to one another. Such oligomers include, for example, both linear, cyclic, and branched polymers of nucleic acids and peptides, which peptides can have either alpha-, beta-, or omega-amino acids.

The term "oligonucleotide" refers to a single-stranded DNA or RNA molecule or to analogs of either. Suitable oligonucleotides may be prepared by the phosphoramidite method described by Beaucage et al., 1981, *Tetr. Lett.* 22:1859–1862, or by the triester method, according to Matteucci et al., 1981, *J. Am. Chem. Soc.* 103:3185, or by other methods, such as by using commercially available, automated oligonucleotide synthesizers.

The term "operably linked" refers to the placement of one nucleic acid into a functional relationship with another nucleic acid. For instance, a promoter is "operably linked" to a coding sequence if the promoter causes the transcription of the coding sequence. Generally, "operably linked" means that the DNA sequences being linked are contiguous and, where necessary to join two peptide or protein coding regions, in reading frame with one another.

The term "peptide" refers to an oligomer in which the monomers are amino acids (usually alpha-amino acids) joined together through amide bonds. Alternatively, a "peptide" can be referred to as a "polypeptide." Peptides are more than two amino acid monomers long, but more often are more than 5 to 10 amino acid monomers long and can be even longer than 20 amino acids, although peptides longer than 20 amino acids are more likely to be called "polypeptides."

The term "protein" is well known in the art and usually refers to a very large polypeptide, or set of associated polypepides, that has some biological function. For purposes of the present invention the terms "peptide," "polypeptide," and "protein" are largely interchangeable as libraries of all three types can be prepared using substantially similar methodology.

The term "random peptide" refers to an oligomer composed of two or more amino acid monomers and constructed by a means with which one does not entirely preselect the specific sequence of any particular oligomer. The term "random peptide library" refers not only to a set of recombinant DNA vectors that encodes a set of random peptides, but also to the set of random peptides encoded by those vectors, as well as the fusion proteins containing those random peptides. The term "protein library" has a meaning similar to "random peptide library," but the different library members differ with respect to the amino acid sequence of, or coding sequence for, the protein of interest, so that the library serves as a collection of related but different versions of the same protein.

The term "receptor" refers to a molecule that has an affinity for a given ligand. Receptors may be naturally-occurring or synthetic molecules. Receptors can be employed in their unaltered natural or isolated state, in a recombinant or modified form, or as aggregates with other species. Examples of receptors that can be employed in the method of the present invention include, but are not restricted to, antibodies, cell membrane receptors, monoclonal antibodies, antisera reactive with specific antigenic determinants (such as on viruses, cells, or other materials), polynucleotides, nucleic acids, lectins, polysaccharides, cells, cellular membranes, viruses, and organelles. Receptors are sometimes referred to in the art as "anti-ligands." As the term "receptor" is used herein, no difference in meaning is intended. A "ligand-receptor pair" is formed when a receptor and ligand have combined through molecular recognition to form a complex.

The terms "recombinant DNA cloning vector" and "recombinant DNA expression vector" refer to a DNA or RNA molecule that encodes a useful function and can either be used to transform a host cell or be introduced into a cell-free translation system to produce a protein encoded by the vector. For purposes of the present invention, a cloning vector typically serves primarily as an intermediate in the construction of an expression vector; the latter vector is used to transform or transfect a host cell (or is introduced into a cell-free transcription and translation system) so that the transformed host cell (or cell-free transcription and translation system) produces a protein or other product encoded by the vector. Such vectors are typically "plasmids," which, for purposes of the present invention, are vectors that can be extrachromosomally maintained in a host cell, but can also be vectors that integrate into the genome of a host cell. Those of skill in the art may refer to "cloning vectors", as defined herein, as "vectors" and to "expression vectors," as defined herein, as "plasmids."

The term "solid support" refers to a material having a rigid or semi-rigid surface. Such materials will preferably take the form of small beads, pellets, disks, chips, or wafers, although other forms may be used. In some embodiments, at least one surface of the solid support will be substantially flat.

The term "surface" refers to any generally two-dimensional structure on a solid substrate and may have steps, ridges, kinks, terraces, and the like without ceasing to be a surface.

The term "synthetic" refers to production by in vitro chemical or enzymatic synthesis.

II. Methods and Reagents of the Invention

The random peptide generating and screening system known as the "peptides on plasmids" system was used to discover the small, efficient peptide biotinylation sequences of the present invention. The library was constructed to express peptides of the form: $X_{10}$Ile Val X Ala Met Lys Met $X_{10}$ (SEQ. ID NO:2), where X denotes a random residue, the other letters are three letter abbreviations of amino acids, and the underlining indicates slight degeneracy in the codon for the specified amino acids, as described below. This sequence was selected based on the known sequences of several biolinylated proteins (see, Samols et al., 1988, *J. Biol Chem.* 263:6461–6464, incorporated herein by reference) as shown in Table 1. As denoted by the ellipses, the sequences below are only portions of the large sequences believed, prior to the present invention, to be necessary for biotinylation.

TABLE 1

| | |
|---|---|
| TC 1.3S | ... Gly Gln Thr Val Leu Val Leu Glu Ala Met Lys Met Glu Thr Glu Ile Asn Ala Pro Thr Asp Gly ... (SEQ. ID NO:3) |
| OADC | ... Gly Glu Val Leu Leu Ile Leu Glu Ala Met Lys Met Glu Thr Glu Ile Arg Ala Ala Gln Ala Gln ... (SEQ. ID NO:4) |
| cACC | ... Gly Gln Cys Phe Ala Glu Ile Glu Val Met Lys Met Val Met Thr Leu Thr Ala Gly Glu Ser Gly ... (SEQ. ID NO:5) |
| EcBCCP | ... Gly Asn Thr Leu Cys Ile Val Glu Ala Met Lys Met Met Asn Gln Ile Glu Ala Asp Lys Ser Gly ... (SEQ. ID NO:6) |
| yPC | ... Gly Gln Pro Val Ala Val Leu Ser Ala Met Lys Met Glu Met Ile Ile Ser Ser Pro Ser Asp Gly ... (SEQ. ID NO:7) |
| hPC | ... Gly Gln Pro Leu Cys Val Leu Ser Ala Met Lys Met Glu Thr Val Val Thr Ser Pro Met Glu Gly ... (SEQ. ID NO:8) |
| sPC | ... Gly Gln Pro Leu Val Leu Ser Ala Met Lys Met Glu Thr Val Val Thr Ser Pro Val Thr Glu (SEQ. ID NO:9) |
| aPC | ... Gly Ala Pro Leu Val Leu Ser Ala Met Lys Met Glu Thr Val Val Thr Ala Pro Arg ... (SEQ. ID NO:10) |
| hPCC | ... Gly Gln Glu Ile Cys Val Ile Glu Ala Met Lys Met Gln Asn Ser Met Thr Ala Gly Lys Thr Gly ... (SEQ. ID NO:11) |
| tbp | ... Gly Gln Pro Val Leu Val Leu Glu Ala Met Lys Met Glu His Val Val Lys Ala Pro Ala Asn Gly ... (SEQ. ID NO:12) |

The lysine residue that becomes biotinylated is contained within the "AlaMetLysMet" (SEQ. ID NO:13) sequence common to most of the proteins in Table 1, which are the 1.3S submit of *Propionibacterium shermanii* branscarboxylase (TC 1.3S); the Klebsiella oxaloacetate decarboxylase (OADC); chicken acetyl-CoA carboxylase (cACC); the *E. coli* acetyl-CoA carboxylase (EcBCCP); the yeast pyruvate carboxylase (yPC); the human pyruvate carboxylase (hPC); the sheep pyruvate carboxylase (sPC); the rat pyruvate carboxylase (aPC); the human propionyl-CoA carboxylase (hPCC); and the tomato biotinyl peptide (tbp). The sequences of these proteins share several conserved residues and/or regions having similar properties (e.g., branched chain amino acids or amidated acids).

Despite this teaching that a large region is required for biotinylation, the peptides on plasmids library used to discover the biotinylation peptides of the present invention was designed to display random peptides only 27 amino acids long, containing only one fixed codon (for Lys) and 5 conserved codons (for the underlined amino acids above). Conserved codons were prepared by programming the oligonucleotide synthesizer to add, for each nucleotide of a conserved codon, 91% of the correct nucleotide and 3% each of the three other nucleotides. By this method, a very large library of random peptides was prepared and used to transform *E. coli* host cells. The peptides encoded by each clone of these libraries were fused to the carboxy-terminus of the sequence-specific DNA binding lac repressor protein (LacI). Each library particle consists of a LacI-peptide fusion bound to the lac operator (lacO) sites on the same plasmid that encoded it. Expression of these libraries in the cytoplasm allows the cells to provide compartmentalization, so that each fusion protein is bound to the appropriate plasmid.

Because the peptides on plasmids library particles are cytoplasmic, the random peptide region has access to the BirA enzyme in *E. coli* host cells. Any random peptides that productively interact with BirA (presumably a small fraction of the total) become biotinylated. After cell lysis, the biotinylated library, particles were isolated by binding to immobilized streptavidin. The background of peptide sequences that bind to streptavidin in the absence of biotinylation (see Devlin at el., 1990, *Science* 249: 404–406, incorporated herein by reference) were eliminated by adding free biotin competitor after allowing the library particles to bind to the immobilized streptavidin. The affinity of these background peptides for streptavidin is lower than the affinity of biotin, and so background peptides are displaced by the free biotin. The desired biotinylated peptides were not displaced by biotin, because those peptides are allowed to bind first, have an affinity similar to that of biotin, and interact multivalently with the mobilized streptavidin.

Thus, the protocol involved lysing the transformed cells, removing cellular debris by centrifugation, and collecting the crude lysate, from which plasmids encoding biotinylation peptides were isolated by affinity enrichment on streptavidin, as described in the Examples below. This process was repeated three times, starting with the plasmids collected at the end of each previous cycle, with the results shown in Table 2.

TABLE 2

| | Cycle 1 | Cycle 2 | Cycle 3 | Cycle 4 |
|---|---|---|---|---|
| Input plasmids | $6.8 \times 10^{11}$ | $2.3 \times 10^{11}$ | $1.65 \times 10^{11}$ | $8.5 \times 10^{9}$ |
| Recovered plasmids | $7.6 \times 10^{5}$ | $1.4 \times 10^{6}$ | $3.0 \times 10^{6}$ | $1.42 \times 10^{7}$ |
| % Recovered | 0.00011 | 0.006 | 0.0018 | 0.166 |
| Negative Control Recovered Plasmids | N.A. | $3.8 \times 10^{5}$ | $3.8 \times 10^{5}$ | $1.1 \times 10^{6}$ |
| % Recovered (Negative Control) | N.A. | 0.00017 | 0.00022 | 0.013 |
| Enrichment Factor | N.A. | 3.6 | 8 | 13 |

These results indicated flat the library contained members that displayed biotinylation peptides and so could be enriched and identified. Several of the isolates from the fourth round of streptavidin binding were tested to determine whether the displayed peptides directed biotinylation. The sequences of the random peptides in the positive clones are shown in Table 3, ranked in order of the strength of their reaction in an ELISA. The sequences reveal not only residues that tend to move closer to the consensus sequence defined by the known biotinylated proteins but also residues that are different from the known consensus sequence. The peptides do not have sequence motifs (such as HisProGln) that have been associated with weak binding to streptavidin (Devlin et al., supra).

TABLE 3

Leu Glu Glu Val Asp Ser Thr Ser Ser Ala Ile Phe Asp Ala Met Lys
Met Val Trp Ile Ser Pro Thr Glu Phe Arg (SEQ. ID NO:14)
Gln Gly Asp Arg Asp Glu Thr Leu Pro Met Ile Leu Arg Ala Met Lys
Met Glu Val Tyr Asn Pro Gly Gly His Glu Lys (SEQ. ID NO:15)
Ser Lys Cys Ser Tyr Ser His Asp Leu Lys Ile Phe Glu Ala Gln Lys
Met Leu Val His Ser Tyr Leu Arg Val Met Tyr Asn Tyr (SEQ. ID NO:16)
Met Ala Ser Ser Asp Asp Gly Leu Leu Thr Ile Phe Asp Ala Thr Lys
Met Met Phe Ile Arg Thr (SEQ. ID NO:17)
Ser Tyr Met Asp Arg Thr Asp Val Pro Thr Ile Leu Glu Ala Met Lys
Met Glu Leu His Thr Thr Pro Trp Ala Cys Arg (SEQ. ID NO:18)
Ser Phe Pro Pro Ser Leu Pro Asp Lys Asn Ile Phe Glu Ala Met Lys
(SEQ. ID NO:19)
Ser Val Val Pro Glu Pro Gly Trp Asp Gly Pro Phe Glu Ser Met Lys
Met Val Tyr His Ser Gly Ala Gln Ser Gly Gln (SEQ. ID NO:20)
Val Arg His Leu Pro Pro Pro Leu Pro Ala Leu Phe Asp Ala Met
Lys Met Glu Phe Val Thr Ser Val Gln Phe (SEQ. ID NO:21)
Asp Met Thr Met Pro Thr Gly Met Thr Lys Ile Phe Glu Ala Met
Lys Met Glu Val Ser Thr (SEQ. ID NO:22)
Ala Thr Ala Gly Pro Leu His Glu Pro Asp Ile Phe Leu Ala Met
Lys Met Glu Val Val Asp Val Thr Asn Lys Ala Gly Gln (SEQ. ID NO:23)
Ser Met Trp Glu Thr Leu Asn Ala Gln Lys Thr Val Leu Leu (SEQ. ID NO:24)
Ser his Pro Ser Gln Leu Met Thr Asn Asp Ile Phe Glu Gly Met
Lys Met Leu Tyr His (SEQ. ID NO:25)
Ser Ile Glu Arg Gly Gly Ser Thr His Lys Ile Leu Ala Ala Met
Lys Met Tyr Gln Val Ser Thr Pro Ser Cys Ser (SEQ. ID NO:26)
Thr Ser Glu Leu Ser Lys Leu Asp Ala Thr Ile Phe Ala Ala Met
Lys Met Gln Trp Trp Asn Pro Gly (SEQ. ID NO:27)
Val Met Glu Thr Gly Leu Asp Leu Arg Pro Ile Leu Thr Gly Met
Lys Met Asp Trp Ile Pro Lys (SEQ. ID NO:28)

The sequences of the biotinylated clones from the first library, shown in Table 3, are aligned at the presumably modified Lys residue. Several clones were present more than once in the set of 20 sequences obtained, so only 15 independent sequences are shown. At some positions in the sequences, no clear consensus is apparent. At other residues, however, clear trends emerge. For example, position −4 (relative to the Lys residue) was designed to encode Val to match that residue of *E. coli* biotin carboxyl carrier protein (GTT codon with each base synthesized 91% as designated, 3% each of the other bases). In spite of this very light mutagenesis, every sequence had a mutation that changed the encoded amino add to either Leu or Phe. Leu is the residue found at this position in most of the naturally biotinylated sequences from organisms other than *E. coli*, but Phe was not present in the sequences examined. Residue −3, encoded in the library by a random (NNK) codon, was negatively charged (Glu or Asp) in 9 of the 15 sequences. Again, this consensus sequence is similar to that found in the naturally occurring sequences (Glu or Set). The +3 position, however, defines a new consensus not found in the natural sequences. 15 of the 15 peptides had a hydrophobic residue (Trp, Tyr, Val, Phe, or Leu) at +3, instead of the most commonly found Thr from the enzyme sequences.

Perhaps the most revealing sequence from the first library was Ser Met Trp Glu Thr Leu Asn Ale Gln Lys Thr Val Leu Leu (SEQ. ID NO:24), which arose from a single base deletion during synthesis or cloning of the library oligonucleotide. This sequence matches only three residues in the enzyme consensus sequence, but does fit the pattern of the other library clones at positions +2 and +3. These results show that the evolutionary constraints on the enzyme sequence result from a combination of factors, only one of which is the ability to be biotinylated.

To define more clearly the consensus sequence for biotinylation, three additional libraries were screened (see Tables 4, 5, and 6, below). Two were based on the pattern from the clones isolated from the first library, and the other consisted simply of a Lys residue flanked on both sides by 10 random residues. After four rounds of panning, a restriction fragment containing the random region was subcloned from the pool of enriched clones into an MBP (melrose binding protein) expression vector (see U.S. patent application Ser. No. 876,288, filed Apr. 29, 1992, incorporated herein by reference). These populations of plasmids were then screened using a colony lift technique involving detection with a streptavidin-alkaline phosphatase conjugate. The biolinylation of several of these clones was confirmed by labeling with $^3$H-biotin.

The second library was constructed with a random peptide coding sequence defined by Xaa Xaa Xaa Ile Phe Glu Ala Met Lys Met Xaa Xaa Xaa Xaa Xaa (SEQ. ID NO:29); where Xaa is an NNK codon, underlined single residues are codons for the amino add shown but with a 70/10/10/10 mutagenesis mixture (70% of the base that encodes the amino acid at a particular position in the codon and 10% each of the other three bases), and the codon for Lys is fixed. The biotinylated sequences isolated and sequenced from this library are shown in Table 4.

TABLE 4

Leu His His Ile Leu Asp Ala Gln Lys Met Val Trp Asn His Arg
(SEQ ID NO:30)
Pro Gln Gly Ile Phe Glu Ala Gln Lys Met Leu Trp Arg Ser
(SEQ ID NO:31)
Leu Ala Gly Thr Phe Glu Ala Leu Lys Met Ala Trp His Glu His
(SEQ ID NO:32)
Leu Asn Ala Ile Phe Glu Ala Met Lys Met Glu Tyr Ser Gly
(SEQ ID NO:33)
Leu Gly Gly Ile Phe Glu Ala Met Lys Met Glu Leu Arg Asp
(SEQ ID NO:34)
Leu Leu Arg Thr Phe Glu Ala Met Lys Met Asp Trp Arg Asn Gly
(SEQ ID NO:35)
Leu Ser Thr Ile Met Glu Gly Met Lys Met Tyr Ile Gln Arg Ser
(SEQ ID NO:36)
Leu Ser Asp Ile Phe Glu Ala Met Lys Met Val Tyr Arg Pro Cys
(SEQ ID NO:37)
Leu Glu Ser Met Leu Glu Ala Met Lys Met Gln Trp Asn Pro Gln
(SEQ ID NO:38)
Leu Ser Asp Ile Phe Asp Ala Met Lys Met Val Tyr Arg Pro Gln
(SEQ ID NO:39)
Leu Ala Pro Phe Phe Glu Ser Met Lys Met Val Trp Arg Glu His
(SEQ ID NO:40)
Leu Lys Gly Ile Phe Glu Ala Met Lys Met Glu Tyr Thr Ala Met
(SEQ ID NO:41)
Leu Glu Gly Ile Phe Glu Ala Met Lys Met Glu Tyr Ser Asn Ser
(SEQ ID NO:42)
Leu Leu Gln Thr Phe Asp Ala Met Lys Met Glu Trp Leu Pro Lys
(SEQ ID NO:43)
Val Phe Asp Ile Leu Glu Ala Gln Lys Val Val Thr Leu Arg Phe
(SEQ ID NO:44)
Leu Val Ser Met Phe Asp Gly Met Lys Met Glu Trp Lys Thr Leu
(SEQ ID NO:45)
Leu Glu Pro Ile Phe Glu Ala Met Lys Met Asp Trp Arg Leu Glu
(SEQ ID NO:46)
Leu Lys Glu Ile Phe Glu Gly Met Lys Met Glu Phe Val Lys Pro
(SEQ ID NO:47)
Leu Gly Gly Ile Glu Ala Gln Lys Met Leu Leu Tyr Arg Gly Asn
(SEQ ID NO:48)

The third library was constructed with a random peptide coding sequence defined by Xaa Xaa Xaa Xaa Xaa Xaa Ile Phe Glu Ala Met Lys Met Xaa Xaa Xaa Xaa Xaa (SEQ. ID NO:49); where Xaa is an NNK codon, underlined single residues are codons for the amino acid shown but with a 70/10/10/10 mutagenesis mixture (70% of the base that encodes the amino add at a particular position in the codon and 10% each of the other three bases), and the codon for Lys is fixed. The biotinylated sequences isolated and sequenced from this library are shown in Table 5.

TABLE 5

Arg Pro Val Leu Glu Asn Ile Phe Glu Ala Met Lys Met Glu Val Trp Lys Pro (SEQ ID NO:50)
Arg Ser Pro Ile Ala Glu Ile Phe Glu Ala Met Lys Met Glu Tyr Arg Glu Thr (SEQ ID NO:51)
Gln Asp Ser Ile Met Pro Ile Phe Glu Ala Met Lys Met Ser Trp His Val Asn (SEQ ID NO:52)
Asp Gly Val Leu Phe Pro Ile Phe Glu Ala Met Lys Met Ile Arg Leu Glu Thr (SEQ ID NO:53)
Val Ser Arg Thr Met Thr Asn Phe Glu Ala Met Lys Met Ile Tyr His Asp Leu (SEQ ID NO:54)
Asp Val Leu Leu Pro Thr Val Phe Glu Ala Met Lys Met Tyr Ile ThrLys (SEQ ID NO:55)
Pro Asn Asp Leu Glu Arg Ile Phe Asp Ala Met Lys Ile Val Thr Val His Ser (SEQ ID NO:56)
Thr Arg Ala Leu Leu Glu Ile Phe Asp Ala Gln Lys Met Leu Tyr Gln His Leu (SEQ ID NO:57)
Arg Asp Val His Val Gly Ile Phe Glu Ala Met Lys Met Tyr Thr Val Glu Thr (SEQ ID NO:58)
Gly Asp Lys Leu Thr Glu Ile Phe Glu Ala Met Lys Ile Gln Trp Thr Ser Gly (SEQ ID NO:59)
Leu Glu Gly Leu Arg Ala Val Phe Glu Ser Met Lys Met Glu Leu Ala Asp Glu (SEQ ID NO:60)
Val Ala Asp Ser his Asp Thr Phe Ala Ala Met Lys Met Val Trp Leu Asp Thr (SEQ ID NO:61)
Gly Leu Pro Leu Gln Asp Ile Leu Glu Ser Met Lys Ile Val Met Thr Ser Gly (SEQ ID NO:62)
Arg Val Pro Leu Glu Ala Ile Phe Glu Gly Ala Lys Met Ile Trp Val Pro Asn Asn (SEQ ID NO:63)
Pro Met Ile Ser His Lys Asn Phe Glu Ala Met Lys Met Lys Phe Val Pro Glu (SEQ ID NO:64)
Lys Leu Gly Leu Pro Ala Met Phe Glu Ala Met Lys Met Glu Trp His Pro Ser (SEQ ID NO:(SEQ ID NO:65)
Gln Pro Ser Leu Leu Ser Ile Phe Glu Ala Met Lys Met Gln Ala Ser Leu Met (SEQ ID NO:66)
Leu Leu Glu Leu Arg Ser Asn Phe Glu Ala Met Lys Met Glu Trp Gln Ile Ser (SEQ ID NO:67)
Asp glu Glu Leu Asn Gln Ile Phe Glu Ala Met Lys Met Tyr Pro Leu Val His Val Thr Lys (SEQ ID NO:68)

The fourth library was constructed with a random peptide coding sequence defined by Xaa Xaa Xaa Xaa Xaa Xaa Xaa Xaa Xaa Xaa Lys Xaa Xaa Xaa Xaa Xaa Xaa Xaa Xaa Xaa (SEQ. ID NO:69); where Xaa is an NNK codon, and the codon for Lys is fixed. The biotinylated sequences obtained and sequenced from this library are shown in Table 6.

TABLE 6

Ser Asn Leu Val Ser Leu Leu His Ser Gln Lys Ile Leu Trp Thr Asp Pro Gln Ser Phe Gly (SEQ. ID NO:70)
Leu Phe Leu His Asp Phe Leu Asn Ala Gln Lys Val Glu Leu Try Pro Val Thr SerSer Gly (SEQ. ID NO:71)
Ser Asp Ile Asn Ala Leu Leu Ser Thr Gln Lys Ile Tyr Trp ala His (SEQ. ID NO:72)

The biotinylation peptides from these libraries serve to define further the novel consensus sequence for the biotinylation peptides of the present invention. Several features are worth noting. A strong preference for Leu at position −8 is clear, especially in the second library, which had a shorter random sequence region to the left of the modified Lys than any of the other libraries. The other sets of sequences share this preference at −8, but to a lesser extent than in the second library. The Leu at this position may be more important when there are fewer amino acids connecting the biotinylation domain to the carrier protein. There is no consensus in the naturally occurring sequences at this site.

At other positions, many residues are found and only a general trend is apparent. For example, many residues are found at position −6, but not large hydrophobic residues (Leu, Val, Ile, Trp, Phe, or Tyr), a tendency that differs from that of the naturally occurring enzymes (Leu is most frequent). Position +4 contains a wide variety of residues, but with a clear preference for basic amino adds (18 of 56 are Arg, His, or Lys) over acidic residues (no Asp or Glu).

At position −2, a preference for small size is clear, as only Ala, Gly, Set, or Thr are found. Position −1 was biased to be Met in all libraries except the fourth library. In these biased libraries, Met is found most often, but Gln is frequently present. Notably, the mutation from an Met codon (ATG) to a Gln codon (CAA/G) requires two base changes. In the clones that were unbiased at this position, 4 of 4 clones have Gln, indicating that Gln might in fact be the preferred residue. The hydrophobic residues Met, Ile, and Val are found in almost all of the sequences at position +1. Position +2 is often the natural consensus Glu but also tends to contain the hydrophobic residues Leu, Val, Tyr, and Ile.

To explore the general utility of the biotinylation sequences and to expand their possible uses, a library was made so that the biotinylation peptides would be expressed in a fusion protein at the N-terminus of cytoplasmic MBP. This library was heavily biased in favor of sequences that fit the consensus sequence of the invention, with a random peptide defined by Met Ala $Xaa_1$ $Xaa_2$ Leu $Xaa_3$ $Xaa_4$ Ile (Phe/Leu) (Glu/Asp) Ala Gln Lys (Met/Ile) Glu Trp (His/Arg) $Xaa_9$ $Xaa_{10}$ $Xaa_{11}$ Gly Gly Ser (SEQ. ID NO:73), in which the underlined residues are fixed; the underlined residues are 97/1/1/1 mutagenized codons for the residues shown; and $Xaa_{(n)}$ is an NNK codon. The sequences of positive clones from this library identified by colony lifts are shown in Table 7.

TABLE 7

Met ala Ser Ser Leu Arg Gln* Ile Leu Asp Ser Gln Lys Met Glu Trp Arg Ser Asn Ala Gly Gly Ser (SEQ. ID NO:74)
Met Ala His Ser Leu Val Pro Ile Phe Asp Ala Gln Lys Ile Glu Trp Arg Asp Pro Phe Gly Gly Ser (SEQ. ID NO:75)
Met Gly Pro Asp Leu Val Asn Ile Phe Glu Ala Gln Lys Ile Glu Trp His Pro Leu Thr Gly Gly Ser (SEQ. ID NO:76)
Met Ala Phe Ser Leu Arg Ser Ile Leu Glu Ala Gln Lys Met Glu Leu Arg Asn Thr Pro Gly Gly Ser (SEQ. ID NO:77)
Met Ala Gly Gly Leu Asn Asp Ile Phe Glu Ala Gln Lys Ile Glu Trp His Glu Asp Thr Gly Gly Ser (SEQ. ID NO:78)
Met Ser Ser Tyr Leu Ala Pro Ile Phe Glu Ala Gln Lys Ile Glu Trp His Ser Ala Tyr Gly Gly Ser (SEQ. ID NO:79)
Met Ala Lys Ala Leu Gln* Lys Ile Leu Glu Ala Gln Lys Met Glu Trp Arg Ser His Pro Gly Gly Ser (SEQ. ID NO:80)
Met Ala Phe Gln Leu Cys Lys Ile Phe Tyr Ala Gln Lys Met Glu Trp His Gly Val Gly Gly Gly Ser (SEQ. ID NO:81)
Met Ala Gly Ser Leu Ser Thr Ile Phe Asp Ala Gln Lys Ile Glu Trp His Val Gly Lys Gly Gly Ser (SEQ. ID NO:82)
Met Ala Gln Gln Leu Pro Asp Ile Phe Asp Ala Gln Lys Ile Glu Trp Arg Ile Ala Gly Gly Gly Ser (SEQ. ID NO:83)
Met Ala Gln Arg Leu Phe His Ile Leu Asp Ala Gln Lys Ile Glu Trp His Gly Pro Lys Gly Gly Ser (SEQ. ID NO:84)
Met Ala Gly Cys Leu Gly Pro Ile Phe Glu Ala Gln Lys Met Glu Trp Arg His Phe Val Gly Gly Ser (SEQ. ID NO:85)
Met Ala Trp Ser Leu Lys Pro Ile Phe Asp Ala Gln Lys Ile Glu Trp His Ser Pro Gly Gly Gly Ser (SEQ. ID NO:86)
Met Ala Leu Gly Leu Thr Arg Ile Leu Asp Ala Gln Lys Ile Glu Trp His Arg Asp Ser Gly Gly Ser (SEQ. ID NO:87)
Met Ala Gly Ser Leu Arg Gln Ile Leu Asp Ala Gln Lys Ile Glu Trp Arg Arg Pro Leu Gly Gly Ser (SEQ. ID NO:88)

TABLE 7-continued

Met Ala Asp Arg Leu Ala Tyr Ile Leu Glu Ala Gln Lys Met Glu Trp His Pro His Lys Gly Gly Ser (SEQ. ID NO:89)

Gln* = supE suppressed amber codon

The biotinylation of several of these clones was confirmed by labeling with $^3$H-biotin. The ability to express functional biotinylation sequences free at either end of a protein indicates that there is no requirement that either end of the peptide be free in order to interact with the biotin holoenzyme synthetase.

As discussed above, the short, biotinylation peptides of the invention can be biotinylated in vivo or in vitro and can be used for a wide variety of purposes, including purification, immobilization, labeling, and detection of proteins. A few illustrative examples include: (1) labeling receptors with biotin at a defined site, so that the labeled receptor could be, for instance, bound to streptavidin to produce a tetravalent receptor to increase the sensitivity of binding assays, such as those described in U.S. Pat. No. 5,143,854, and U.S. patent application Ser. No. 946,239, filed Sep. 16, 1992, each of which is incorporated herein by reference; (2) labeling fusion proteins containing peptide leads from any screening program, so that the labeled fusion proteins can be used to test binding of the peptide to receptors in a monovalent format (by probing with labeled streptavidin after binding occurs) or in a multivalent format (by prebinding the fusions to labeled streptavidin and then testing binding to receptors or so that the peptides can be mobilized on streptavidin-coated beads or in microtiter wells for probing with receptors, such as protease enzymes, in solution; (3) labeling peptides or proteins directly by growing cells in the presence of tritiated biotin—with a biotin auxotrophs the peptides could be labeled at a known specific activity to permit quantitative measurements of binding activity; and (4) developing technology for doing enzymatic reactions on surfaces by exposing libraries of variant immobilized sequences to BirA, biotin, and ATP, so that those peptides that were substrates would be biotinylated and could be detected with labeled streptavidin.

This invention also embraces kits which are useful for producing proteins containing biotinylation peptides. Such kits comprise, for instance, a recombinant expression polynucleotide which can be used to produce the peptides of the invention fused to a coding sequence of choice, and directions for using the polynucleotides. DNA expression polynucleotides may be destined to replicate episomally or to integrate into the chromosome of the host cell chosen for expression. Frequently, the DNA polynucleotides of the kit contain a multiple cloning site linked to sequence coding for the peptides of the inventions such that any coding sequence may be inserted in the correct translational reading frame for expression. These kits may be used to produce the peptides of the invention fused to the amino terminus the carboxyl terminus or internal to the coding sequence of choice. Within these fusion proteins, the peptides of the invention may be separated from the coding sequences by additional spacer sequences.

Expression of coding sequence will preferably be under control of an inducible promoter; some examples are the lac or tac promoter in *E. coli*, the gal4 promoter in *S. cerevisiae*, the glaA promoter in *Aspergillus niger*, or the murine metallothionein promoter in many mammalian cells. Alternatively, constitutive promoters may be desirable for certain applications, such as the SV40 early promoter in mammalian cells. For some applications, such as in vitro translation in rabbit reticulocytes, the ability to synthesize RNA in vitro using a RNA polymerase such as that from the bacteriophage SP6 will be needed. In that case, signals for initiation of transcription by both SP6 RNA polymerase and an alternative RNA polymerase can be operably linked to the same expression sequence.

Besides a promoter for initiation of the expression sequences, the polynucleotides of the kits will also preferably contain sequences for transcriptional termination, such as the T7 terminator in *E. coli* or the SV40 terminator in mammalian cells. Additionally, when the proteins are expressed in mammalian cells, a signal for polyadenylation is desirable, such as the SV40 poly adenylation sequence.

Of course, additional sequences may also be included in the polynucleotides of these kits which will confer additional properties on the proteins produced. For example, a signal sequence which causes the expressed proteins to be secreted from the cell may be incorporated into the polynucleotides. Sequences which serve to link expressed proteins to the membrane, such as a sequence encoding a hydrophobic membrane spanning domain, or an encoded sequence which signals attachment of a glycosylphosphatidylinositol membrane anchor to the protein, may be included as part of the expression polynucleotide. The polynucleotides may also encode a sequence recognized by a protease, such as factor $X_a$, adjacent to the sequence encoding the biotinylation peptides of the invention. One of skill in the art will recognize that these and many other combinations of additional sequences may be advantageous.

Other constituents of the kits may comprise host cells suitable for obtaining expression from the polynucleotide, avidin or streptavidin coupled to a solid support, avidin or streptavidin coupled to a detectable label such as the enzyme horseradish peroxidase, a biotinylation enzyme such as purified BirA, and instructions for analysis and purification of the proteins expressed using these kits. Preferably, the host cells will express a biotinylating enzyme. Optionally, polynucleotides which, when transformed into host cells, cause the production or overproduction of biotinylating enzymes may be supplied in the kits, or the host cells provided with the kits may be already modified to produce or over-produce biotinylating enzymes. However, for some applications the absence of biotinylating enzyme in the host cell may be advantageous. For example, the kit user may prefer to biotinylate the expressed fusion proteins in vitro.

Those of skill in the art recognize from the description above that the present invention provides many advantages and more application than prior art methods for biotinylating proteins. The biotinylation peptides of the invention are small but specific, allowing one to label a protein at a defined site, at either end of or internally to the protein to be labelled. The invention provides an improved immobilization method, allowing one to avoid the use of antibodies and the problems attendant thereto. The high binding affinity of the avidin-biotin interaction provides advantages for labelling, localization, detection, immobilization, and purification methods as well. For instance, one could use the biotinylation peptides of the invention to purify BirA protein or other biotinylation reaction can occur in vivo (where few other proteins are naturally biotinylated) or in vitro, with readily available materials. As can be appreciated from the disclosure above, the present invention has a wide variety of applications. Accordingly, the following examples are offered by way of illustration, not by way of limitation.

EXAMPLE 1

Library Construction the peptides on plasmids libraries were made in vector pJS142, a derivative of plasmid pMC5 described in U.S.

patent application Ser. No. 963,321, filed Oct. 15, 1992, incorporated herein by reference. This vector is designed to link the random region of a library to lacI through a linker encoding the sequence Val Val His Gly Glu Gln Val Gly Gly Glu Ala Ser Gly Gly Gly (SEQ. ID NO:90), the first library was made by annealing phosphorylated oligonucleotides ON-1396 (GAGGTGGTNNKNNKNNKNNKNNKNN-KNNKNNKNNKNNKatcgttNNKg ctatgAAAatgNNKNN-KNNKNNKNNKNNKNNKNNKNNKTAACTAA GTAAAGC (SEQ. ID NO:91), where lower case letters designate bases synthesized from mixtures of 91% of that base and 3% of each of the other bases, referred to as "91/3/3/3 mutagenesis". N means an equimolar mixture of all 4 bases, and K means an equimolar mixture of G and T), ON-829 (ACCACCTCCGG) (SEQ. ID NO:92), and ON-830 (TTACTTAGTTA) (SEQ. ID NO:93) each at a concentration of 1 µM in 0.1 M NaCl, 50 mM Tris pH 7.4, by heating to 70° for 10 min., and allowing the reaction to cool over several hours to below 15°. The annealed oligonucleotides (5.2 pmol) were ligated to 10 µg (2.6 pmol) of SfiI digested pJS142 in 0.5 mL of 20 mM Tris pH 7.4, 10 mM $MgCl_2$, 0.1 mM BDTA, 1 mM ATP, 50 µg/mL BSA, 2 mM DTT, containing 800 cohesive end units of T4 DNA ligase (New England BioLabs) overnight at 14°. The ligations were then heated to 65° for 10 min. The single stranded gap was filled by addition of 26 units of Sequenase™ 2.0 (United States Biochemical) in the presence of 0.2 mM dNTPs. The DNA was phenol/$CHCl_3$ extracted, precipitated with isopropanol, and used to transform ARI 280 (lon-11 sulA1 hsdR17 Δ(ompT-fepC) ΔclpA319::kan ΔlacI lacZU118 recA::cat) to yield a library of $5 \times 10^8$ independent transformants that was amplified and stored as described in U.S. patent application Ser. No. 963,321, filed Oct. 15, 1992, and Cull et al, 1992, *Proc. Natl. Acad. Sci. USA* 89:1865–1869, each of which is incorporated herein by reference, except that the cells were stored in 35 mM HEPES pH 7.5, 0.1 mM EDTA, 50 mM KCl (HEK buffer).

The second ($5 \times 10^9$ transformants), third ($5 \times 10^9$ transformants), and fourth ($2.2 \times 10^9$ transformants) libraries were constructed as described above using ON-1544 (GAGGTGGTNNKNNKNNKatctttgaagctatgAAAatgNN-KNNKNNKNNKNNK TAACTAAGTAAAGC) (SEQ. ID NO:94), where lower case letters designate 70/10/10/10 mutagenesis), ON-1545 (GAGGTGG- TNNKNNKNN-KNNKNNKNNKatctttgaagctatgAAAatgNNKNNK NNKNNKNNKTAACTAAGTAAAGC) (SEQ. ID NO:95), where lower case letters designate 70/10/10/10 mutagenesis), and ON-828 (GAGG- TGGTNNKNNKNN-KNNKNNKNNKNNKNNKNNKNNKAAANNK NNKNNKNNKNNKNNKNNKNNKNNKNNKTAACT-AAGTAAAGC) (SEQ-ID NO:96), respectively, in place of ON-1396. The fourth library was made with 30 µg of vector pJS141, which differs from pJS142 only in that the coding sequence of lacI was altered to encode Ser, Ala, and Ser, respectively, in place of the Cys codons normally found at positions 107, 140, and 281. The library was amplified by transformation of strain ARI 246 (lon-11 sulA1 hsdR17 Δ(ompT-fepC) ΔclpA319::kan lacI42::Tn10 lacZU118).

The fifth library was constructed in the vector pBAD/MBP-N, a derivative of pBAD18, see U.S. patent application Ser. No. 965,677, filed Oct. 22, 1992, incorporated herein by reference, that places a polylinker and the coding sequence for amino acids 27–393 of MBP downstream from the arabinose-inducible araB promoter. The library was made by ligating annealed ON-1699 (CTAGCTAACTAATGGAGGATACATAAATGgctNNK-NNKctgNNKNVKatttt NgaNgctcarAAAat-NgaatggcryNNKNNIQNNKGGTGGTAGCC) (SEQ. ID NO:97), where lower case letters designate 97/1/1/1 mutagenesis; V=A, C, or G; r=g or a; y=c, t), ON-1700 (TCCTCCATTAGTYAG) (SEQ. ID NO:98), and ON-1701 (TCGAGGCTACCACC) (SEQ. ID NO:99) to NheI-XhoI digested pBAD/MBP-N, as described above. The library was used to transform XL1-Blue (F' proAB lacIq lacZΔM15 Tn10(tetR)//recA1 endA1 gyrA96 thi hsdR17 supE44 relA1 lac, Stratagene) and screened by colony lifts as described below.

EXAMPLE 2

Panning

About 2 mL of thawed cells in HEK were added to 6 mL of 25 mM HEPES pH 7.5, 0.07 mM EDTA, 8.3% glycerol, 1.25 mg/mL BSA, 0.83 mM DTT, and 0.2 mM PMSF. The cells were lysed for 2 to 4 min. on ice by the addition of 0.15 mL of 10 mg/mL lysozyme (Boehringer Mannheim), and then, 2 mL of 20% lactose and 0.25 ml of 2 M KCl were added. The supernatant from a 15 min., 27,000×g centrifugation was added to 0.1 mL of streptavidin-agarose beads (Pierce) in 1 mL HEK, 0.2 M lactose (HEKL), 4.5% BSA, 0.9 mg/mL herring DNA and mixed gently at 4° for 1 hour. The beads were centrifuged and washed 4 times with HEKL buffer, 1% BSA, and 0.1 mg/mL herring DNA at 4° (in later rounds, these washes sometimes contained 10 µM biotin) and then incubated for 30 min. at 4° in the same buffer plus 10 µM biotin. The beads were washed 5 times with HEKL buffer, 1% BSA, twice with HEKL buffer, and once or twice with HEK buffer at 4°. The bound plasmids were eluted with 35 mM HEPES pH 7.5, 0.1 mM EDTA, 200 mM KCl, 1 mM IPTG, 10 µg/mL self-annealed ON-413 (GAATTCAATTGTGAGCGCTCACAATTGAATTC) (SEQ. ID NO:100) for 30 min. at room temperature, precipitated with isopropanol, and then used to electrotransform either ARI 280 or ARI 298 (lon-11 sulA1 hsdR17 Δ(ompT-fepC) ΔclpA319::kan ΔlacI lacZU118 recA::cat cytR) for amplification.

EXAMPLE 3

Subcloning into MBP Vector

Plasmids recovered from panning were digested with BspEI and ScaI, and a fragment containing the peptide coding sequence was subcloned into AgeI, ScaI, digested plasmid pELM3, a derivative of pMALc2, which is available from New England Biolabs, designed to accept inserts of coding sequence from pJS142. The transferred fragment encodes GGG-peptide and is linked to the MBP coding region through sequence encoding $Asn_{10}$ Leu Gly Ile Glu Gly Arg Thr. The MBF is retained in the cytoplasm due to the lack of a signal sequence.

EXAMPLE 4

Labeling with $^3H$-biotin

Cells were grown at 37° overnight in minimal medium E (Davis, 1980, *Advanced Bacterial Genetics* (CSH Press)) with 0.4% glycerol, 0.1% vitamin assay casamino acids (Difco), 1 µg/mL thiamine, and 50 µg/mL ampicillin. The cultures were diluted 1/10 in the same medium, grown for several hours, and then added to an equal volume of medium containing 2 µCi/mL $^3H$-Biotin (Amersham) and 0.6 mM IPTG (for pELM3 clones) or 0.4% L-arabinose instead of glycerol (for pBAD/MBP-N clones). Growth was continued for an additional several hours, and then the cells were harvested and lysed with SDS protein gel buffer. The samples were run on a 4–20% gradient acrylamide gel, and fluorographed using Amplify (Amersham) and X-ray film.

EXAMPLE 5

Colony Lifts

Colony lifts were performed in duplicates essentially as described (Sambrook, 1989, *Molecular Cloning: A Laboratory Manual* (CSH Press)), except that the inducing plates contained 10 µm biotin and 0.3 mM IPTG (for pELM3 clones) or 0.2% L-arabinose (for pBAD/MBP-N clones). The blocking agent was 5% BSA, and the probe was 1/5000 diluted streptavidin-alkaline phosphatase conjugate (Gibco BRL).

EXAMPLE 6

Overexpression of BirA

The birA gene was cloned under the control of inducible promoters on two different plasmids. The birA gene was amplified from the plasmid pBA22 (see Barker and Campbell, 1981, J. Mol. Biol. 146:469–492) using primers ON-1589 (SEQ. ID NO:101) (5'TAC AGT GCT AGC TAA CTA ATG GAG GAT ACA TAA ATG AAG GAT AAC ACC GTG CCA CTG 3') and ON-1590 (SEQ. ID NO:102) (5' GTA TCA GAG CTC TTA TTT TTC TGC ACT ACG GAG GGA 3') in a polymerase chain reaction (PCR). The fragment was digested with SacI and NheI and cloned into SacI, NheI digested plasmid pJSIOO, placing birA under control of the araBAD promoter. The resulting plasmid, called pJS170, contains a pBR322-derived replication origin, an ampicillin resistance gene, and the araC gene, which encodes a regulator of the araBAD promoter. Induction of birA expression from this plasmid in LB+0.2% arabinose allows expression of large amounts of BirA protein.

The birA gene fragment was also subcloned into SacI, SpeI digested plasmid pIQCAT-LC9. This places birA under control of the tac promoter, which is inducible with IPTG. This plasmid, called pJS169, also contains a p15A replication origin, a chloramphenicol resistance gene, and the lacIQ allele of the lacI gene, which encodes a repressor of the lac or tac promoters. The p15A replication origin permits this plasmid to replicate in the same cell as pBR322-derived plasmids. Thus, BirA can be overexpressed in the same cell that is expressing the biotinylation target. Cells carrying pJS169 grown in LB+0.3 mM IPTG overexpress BirA to a lesser extent than cells carrying pJS170 induced with 0.2% arabinose.

EXAMPLE 7

Enhanced Biotinylation in an *E. coli* strain overproducing BirA

The efficiency of MBP-peptide fusion biotinylation was determined under two growth condition using a band shift assay. This assay was performed by mixing deglycosylated avidin (UltraAvidin, Leinco Technologies) with a crude cell lysate from an *E. coli* strain that overexpressed the MBP-peptide fusion. The mix was electrophoresed on a 4–20% acrylamide nondenaturing gel compared to the lysate without avidin. Comparison of the two lanes permitted quantitation of the efficiency of biotinylation by observation of the band shift caused by the added avidin. Fusion proteins expressed in a strain carrying pJS169 (with birA induced with 0.3 mM IPTG) in LB media containing 10 µM biotin were biotinylated to a greater extent than those expressed in the absence of extra BirA and added biotin.

In a related experiment, a plasmid carrying biotinylation peptide/MBP fusion proteins under arabinose promoter control, were expressed in a strain also carrying the pJS169 plasmid (with birA). The strain was grown to a cell density of about 0.20.D. Abs$^{600}$, in LB plus 100 µg/ml ampicillin, 30 µg/ml chloramphenicol; 10 µM biotin. Parallel cultures of the strain were then induced under two separate conditions, the first being 0.2% L-arabinose plus 0.3 mM IPTG, and the second being 0.2% L-arabinose, alone. The cells were grown an additional 135 minutes and harvested. Purification of protein from these cultures was carried out in parallel on monovalent avidin columns. SDS-PAGE analysis of the purified product indicated that the concentration of biotinylated MBP fusion protein was greater in the culture induced with L-arabinose, alone. This result indicates that biotinylation of the fusion protein can occur with little or no exogenous induction of birA expression, suggesting that mere catalytic amounts of birA are sufficient for biotinylation.

EXAMPLE 8

Biotinylation of recombinant proteins in vitro

1. BirA overexpression and purification

BirA can be purified either by published procedures (see Buoncristiani and Otsuka, 1988, J. Biol. Chem. 263(2) :1013–1016), or by the following procedure.

A single colony of *E. coli*. strain BL21 transformed with pJS169 was grown overnight in 50 mls of LB+ampicillin. This culture was inoculated 1:100 into 1 liter of LB+ampicillin and grown at 37° C. with shaking until the OD$_{600}$=0.5. After induction with 0.4 mM IPTG, the cells were grown an additional 4 hours, harvested by centrifugation, resuspended in 20 mm Tris-HCl pH 7.4+5 mm DTT (TD5), and lysed by sonication. Cellular debris was removed by centrifugation and the supernatant diluted to 100 ml total volume with TD5 buffer.

Crude supernatant was loaded onto a 10 ml Blue Sepharose FF column (Pharmacia) and washed through with TD (20 mm Tris-HCl pH 7.4) until the A280 of the column flow-through was about 0. This column was eluted with a 100 ml gradient of 0–1.5 M NaCl in TD and 2 ml fractions collected. BirA-containing fractions were pooled and dialyzed against TD until the NaCl concentration was about 15 mM.

The dialysate was concentrated using an Amicon YM30, and then loaded over 5 ml S Sepharose FF column (Pharmacia) and washed through with TD1 (20 mm Tris-HCl pH 7.4+1 mM DTT). Protein was eluted with a 50 ml gradient of 0–350 mM NaCl in TD1.

BirA-containing fractions were pooled, bound to a Biotin-sepharose column, washed with TD1/150 mM NaCl, and eluted with TD1/150 mM NaCl+2 mm biotin. BirA-containing fractions were dialyzed over YM30 against TD1/150 mM NaCl to a final volume of 10 ml.

2. Biotinylation in vitro using purified BirA enzyme.

Proteins fused to one of the peptides of the invention were biotinylated in vitro at 37° C. in a buffer containing: RPMI medium 1640 (Gibco-BRL) supplemented with 5 mπM ATP, 5 mM MgCl$_2$, and 10 μM biotin.

Although the foregoing invention has been described in some detail by way of illustration and example for purposes of clarity and understanding, it will be apparent that certain changes and modifications may be practiced within the scope of the appended claims.

---

What is claimed is:

1. A biotinylation peptide comprising:

a non-naturally occurring peptide sequence of 13 to 50 amino acid residues comprising the sequence:

Leu $Xaa_1$ $Xaa_2$ Ile $Xaa_3$ $Xaa_4$ $Xaa_5$ $Xaa_6$ Lys $Xaa_7$ $Xaa_8$ $Xaa_9$ $Xaa_{10}$ (SEQ ID NO:1), where $Xaa_1$ is any amino acid;
$Xaa_2$ is any amino acid other than Leu, Val, Ile, Trp, Phe, or Tyr;
$Xaa_3$ is Phe or Leu;
$Xaa_4$ is Glu or Asp;
$Xaa_5$ is Ala, Gly, Ser, or Thr;
$Xaa_6$ is Gln or Met;
$Xaa_7$ is Ile, Met, or Val;
$Xaa_8$ is Glu, Leu, Val, Tyr, or Ile;
$Xaa_9$ is Trp, Tyr, Val, Phe, Leu, or Ile; and
$Xaa_{10}$ is any amino acid other than Asp or Glu, wherein said biotinylation-peptide is capable of being biotinylated by a biotin ligase at the lysine residue adjacent to $Xaa_6$.

2. The peptide of claim 1:

wherein said biotinylation sequence has been biotinylated by a biotin ligase.

3. The biotinylation peptide of claim 1, selected from the group consisting of

Leu Glu Glu Val Asp Ser Thr Ser Ser Ala Ile Phe Asp Ala Met Lys Met Val Trp Ile Ser Pro Thr Glu Phe Arg (SEQ ID NO:14);
Gln Gly Asp Arg Asp Gly Thr Leu Pro Met Ile Leu Arg Ala Met Lys Met Glu Val Tyr Asn Pro Gly Gly His Glu Lys (SEQ ID NO:15);
Ser Lys Cys Ser Tyr Ser His Asp Leu Lys Ile Phe Glu Ala Gln Lys Met Leu Val His Ser Tyr Leu Arg Val Met Tyr Asn Tyr (SEQ ID NO:16);
Met Ala Ser Ser Asp Asp Gly Leu Leu Thr Ile Phe Asp Ala Thr Lys Met Met Phe Ile Arg Thr (SEQ ID NO:17);
Ser Tyr Met Asp Arg Thr Asp Val Pro Thr Ile Leu Glu Ala Met Lys Met Glu Leu His Thr Thr Pro Trp Ala Cys Arg (SEQ ID NO:18);
Ser Phe Pro Pro Ser Leu Pro Asp Lys Asn Ile Phe Glu Ala Met Lys Met Tyr Val Ile Thr (SEQ ID NO:19);
Ser Val Val Pro Glu Pro Gly Trp Asp Gly Pro Phe Glu Ser Met Lys Met Val Tyr His Ser Gly Ala Gln Ser Gly Gln (SEQ ID NO:20);
Val Arg His Leu Pro Pro Pro Leu Pro Ala Leu Phe Asp Ala Met Lys Met Glu Phe Val Thr Ser Val Gln Phe (SEQ ID NO:21);
Asp Met Thr Met Pro Thr Gly Met Thr Lys Ile Phe Glu Ala Met Lys Met Glu Val Ser Thr (SEQ ID NO:22);
Ala Thr Ala Gly Pro Leu His Glu Pro Asp Ile Phe Leu Ala Met Lys Met Glu Val Val Asp Val Thr Asn Lys Ala Gly Gln (SEQ ID NO:23);
Ser Met Trp Glu Thr Leu Asn Ala Gln Lys Thr Val Leu Leu (SEQ ID NO:24);
Ser His Pro Ser Gln Leu Met Thr Asn Asp Ile Phe Glu Gly Met Lys Met Leu Tyr His (SEQ ID NO:25);
Thr Ser Glu Leu Ser Lys Leu Asp Ala Thr Ile Phe Ala Ala Met Lys Met Gln Trp Trp Asn Pro Gly (SEQ ID NO:27);
Val Met Glu Thr Gly Leu Asp Leu Arg Pro Ile Leu Thr Gly Met Lys Met Asp Trp Ile Pro Lys (SEQ ID NO:28);
Leu His His Ile Leu Asp Ala Gln Lys Met Val Trp Asn His Arg (SEQ ID NO:30);
Pro Gln Gly Ile Phe Glu Ala Gln Lys Met Leu Trp Arg Ser (SEQ ID NO:31);
Leu Ala Gly Thr Phe Glu Ala Leu Lys Met Ala Trp His Glu His (SEQ ID NO:32);
Leu Asn Ala Ile Phe Glu Ala Met Lys Met glu Tyr Ser Gly (SEQ ID NO:33);
Leu Gly Gly Ile Phe Glu Ala Met Lys Met Glu Leu Arg Asp (SEQ ID NO:34);
Leu Leu Arg Thr Phe Glu Ala Met Lys Met Asp Trp Arg Asn Gly (SEQ ID NO:35);
Leu Ser Thr Ile Met Glu Gly Met Lys Met Tyr Ile Gln Arg Ser (SEQ ID NO:36);
Leu Ser Asp Ile Phe Glu Ala Met Lys Met Val Tyr Arg Pro Cys (SEQ ID NO:37);
Leu Glu Ser Met Leu Glu Ala Met Lys Met Gln Trp Asn Pro Gln (SEQ ID NO:38);
Leu Ser Asp Ile Phe Asp Ala Met Lys Met Val Tyr Arg Pro Gln (SEQ ID NO:39);
Leu Ala Pro Phe Phe Gly Ser Met Lys Met Val Trp Arg Glu His (SEQ ID NO:40);
Leu Lys Gly Ile Phe Glu Ala Met Lys Met Gly Tyr Thr Ala Met (SEQ ID NO:41);
Leu Glu Gly Ile Phe Glu Ala Met Lys Met Glu Tyr Ser Asn Ser (SEQ ID NO:42);
Leu Leu Gln Thr Phe Asp Ala Met Lys Met Glu Trp Leu Pro Lys (SEQ ID NO:43);
Val Phe Asp Ile Leu Glu Ala Gln Lys Val Val Thr Leu Arg Phe (SEQ ID NO:44);
Leu Val Ser Met Phe Asp Gly Met Lys Met Glu Trp Lys Thr Leu (SEQ ID NO:45);
Leu Glu Pro Ile Phe Glu Ala Met Lys Met Asp Trp Arg Leu Glu (SEQ ID NO:46);
Leu Lys Glu Ile Phe Glu Gly Met Lys Met Glu Phe Val Lys Pro (SEQ ID -continued NO:47);
Leu Gly Gly Ile Glu Ala Gln Lys Met Leu Leu Tyr Arg Gly Asn (SEQ ID NO:48);
Arg Pro Val Leu Glu Asn Ile Phe Glu Ala Met Lys Met Glu Val Trp Lys Pro (SEQ ID NO:50);
Arg Ser Pro Ile Ala Glu Ile Phe Glu Ala Met Lys Met Glu Tyr Arg Glu Thr (SEQ ID NO:51);
Gln Asp Ser Ile Met Pro Ile Phe Glu Ala Met Lys Met Ser Trp His Val Asn (SEQ ID NO:52);
Asp Gly Val Leu Phe Pro Ile Phe Glu Ala Met Lys Met Ile Arg Leu Glu Thr (SEQ ID NO:53);
Val Ser Arg Thr Met Thr Asn Phe Glu Ala Met Lys Met Ile Tyr His Asp Leu (SEQ ID NO:54);
Asp Val Leu Leu Pro Thr Val Phe Glu Ala Met Lys Met Tyr Ile Thr Lys (SEQ ID NO:55);
Pro Asn Asp Leu Glu Arg Ile Phe Asp Ala Met Lys Ile Val Thr Val His Ser (SEQ ID NO:56);
Thr Arg Ala Leu Leu Glu Ile Phe Asp Ala Gln Lys Met Leu Tyr Gln His Leu (SEQ ID NO:57);
Arg Asp Val His Val Gly Ile Phe Glu Ala Met Lys Met Tyr Thr Val Glu Thr (SEQ ID NO:58);
Gly AspLys Leu Thr Glu Ile Phe Glu Ala Met Lys Ile Gln Trp Thr Ser Gly (SEQ ID NO:59);
Leu Glu Gly Leu Arg Ala Val Phe Glu Ser Met Lys Met Glu Leu Ala Asp Glu (SEQ ID NO:60);
Val Ala Asp Ser His Asp Thr Phe Ala Ala Met Lys Met Val Trp Leu Asp Thr (SEQ ID NO:61);
Gly Leu Pro Leu Gln Asp Ile Leu Glu Ser Met Lys Ile Val Met Thr Ser Gly (SEQ ID NO:62);
Arg Val Pro Leu Glu Ala Ile Phe Glu Gly Ala Lys Met Ile Trp Val Pro Asn Asn (SEQ ID NO:63);
Pro Met Ile Ser His Lys Asn Phe Glu Ala Met lys Met Lys Phe Val Pro Glu (SEQ ID NO:64);
Lys Leu Gly Leu Pro Ala Met Phe Glu Ala Met Lys Met Glu Trp His Pro Ser (SEQ ID NO:65);
Gln Pro Ser Leu Leu Ser Ile Phe Glu Ala Met Lys Met Gln Ala Ser Leu Met (SEQ ID NO:66);
Leu Leu Glu Leu Arg Ser Asn Phe Glu Ala Met Lys Met Glu Trp Gln Ile Ser (SEQ ID NO:67);
Asp Glu Glu Leu Asn Gln Ile Phe Glu Ala Met Lys Met Tyr Pro Leu Val His Val Thr Lys (SEQ ID NO:68);
Ser Asn Leu Val Ser Leu Leu His Ser Gln Lys Ile Leu Trp Thr Asp Pro Gln Ser Phe Gly (SEQ ID NO:70);
Leu Phe Leu His Asp Phe Leu Asn Ala Gln Lys Val Glu Leu Try Pro Val Thr Ser Ser Gly (SEQ ID NO:71);
Ser Asp Ile Asn Ala Leu Leu Ser Thr Gln Lys Ile Tyr Trp Ala His (SEQ ID NO:72);
Met Ala Ser Ser Leu Arg Gln Ile Leu Asp Ser Gln Lys Met Glu Trp Arg Ser Asn Ala Gly Gly Ser (SEQ ID NO:73);
Met Ala His Ser Leu Val Pro Ile Phe Asp Ala Gln Lys Ile Glu Trp Art Asp Pro Phe Gly Gly Ser (SEQ ID NO:75);

-continued

Met Gly Pro Asp Leu Val Asn Ile Phe Glu Ala Gln Lys Ile Glu Trp His Pro Leu Thr Gly Gly Ser (SEQ ID NO:76);
Met Ala Phe Ser Leu Arg Ser Ile Leu Glu Ala Gln Lys Met Glu Leu Arg Asn Thr Pro Gly Gly Ser (SEQ ID NO:77);
Met Ala Gly Gly Leu Glu Asn Asp Ile Phe Glu Ala Gln Lys Ile Glu Trp His Glu Asp Thr Gly Gly Ser (SEQ ID NO:78);
Met Ser Ser Tyr Leu Ala Pro Ile Phe Glu Ala Gln Lys Ile Glu Trp His Ser Ala Tyr Gly Gly Ser (SEQ ID NO:79);
Met Ala Lys Ala Leu Gln Lys Ile Leu Glu Ala Gln Lys Met Glu Trp Arg Ser His Pro Gly Gly Ser (SEQ ID NO:80);
Met Ala Phe Gln Leu Cys Lys Ile Phe Try Ala Gln Lys Met Glu Trp His Gly Val Gly Gly Gly Ser (SEQ ID NO:81);
Met Ala Gly Ser Leu Ser Thr Ile Phe Asp Ala Gln Lys Ile Glu Trp His Val Gly Lys Gly Gly Ser (SEQ ID NO:82);
Met Ala Gln Gln Leu Pro Asp Ile Phe Asp Ala Gln Lys Ile Glu Trp Arg Ile Ala Gly Gly Gly Ser (SEQ ID NO:83);
Met Ala Gln Arg Leu Phe His Ile Leu Asp Ala Gln Lys Ile Glu Trp His Gly Pro Lys Gly Gly Ser (SEQ ID NO:84);
Met Ala Gly Cys Leu Gly Pro Ile Phe Glu Ala Gln Lys Met Glu trp Arg His Phe Val Gly Gly Ser (SEQ ID NO:85);
Met Ala Trp Ser Leu Lys Pro Ile Phe Asp Ala Gln Lys Ile Glu Trp His Ser Pro Gly Gly Gly Ser (SEQ ID NO:86);
Met Ala Leu Gly Leu Thr Arg Ile Leu Asp Ala Gln Lys Ile Glu Trp His Arg Asp Ser Gly Gly Ser (SEQ ID NO:87);
Met Ala gly Ser Leu Arg Gln Ile Leu Asp Ala Gln Lys Ile Glu Trp Arg Arg Pro Leu Gly Gly Ser (SEQ ID NO:88), and;
Met Ala Asp Arg Leu Ala Tyr Ile Leu Glu Ala Gln Lys Met Glu Trp His Pro His Lys Gly Gly Ser (SEQ ID NO:89).

4. The peptide of claim 3 or claim 2, wherein
either the carboxyl or amino terminus of said biotinylation peptide is covalently coupled to a protein that is incapable of being biotinylated by a biotin-ligase.

5. The peptide of claim 3, claim 1 or claim 2:
wherein the carboxyl terminus of said biotinylation peptide is covalently coupled to
a first protein that is incapable of being biotinylated by a biotin ligase, and
wherein the amino terminus of said biotinylation peptide is coupled to
a second protein that is incapable of being biotinylated by a biotin ligase.

6. The peptide of claim 3, claim 1, or 2 wherein said biotin ligase is BirA.

* * * * *